US009944914B2

(12) United States Patent
Suda et al.

(10) Patent No.: US 9,944,914 B2
(45) Date of Patent: Apr. 17, 2018

(54) METHOD FOR OBTAINING NATURAL VARIANT OF ENZYME AND SUPER THERMOSTABLE CELLOBIOHYDROLASE

(71) Applicant: HONDA MOTOR CO., LTD., Minato-Ku, Tokyo (JP)

(72) Inventors: Migiwa Suda, Wako (JP); Jiro Okuma, Wako (JP); Asuka Yamaguchi, Wako (JP); Yoshitsugu Hirose, Wako (JP); Yasuhiro Kondo, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 0 days.

(21) Appl. No.: 14/643,514

(22) Filed: Mar. 10, 2015

(65) Prior Publication Data
US 2015/0259659 A1    Sep. 17, 2015

(30) Foreign Application Priority Data

Mar. 13, 2014  (JP) ................. 2014-050083

(51) Int. Cl.
| C12N 1/21 | (2006.01) |
| C12N 9/24 | (2006.01) |
| C12N 15/55 | (2006.01) |
| C12P 19/02 | (2006.01) |
| C12N 9/42 | (2006.01) |
| C12P 19/14 | (2006.01) |
| C12N 15/10 | (2006.01) |
| C40B 30/02 | (2006.01) |

(52) U.S. Cl.
CPC ......... *C12N 9/2437* (2013.01); *C12N 15/102* (2013.01); *C12N 15/1034* (2013.01); *C12N 15/1089* (2013.01); *C12P 19/02* (2013.01); *C12P 19/14* (2013.01); *C12Y 302/01004* (2013.01); *C40B 30/02* (2013.01)

(58) Field of Classification Search
None
See application file for complete search history.

(56) References Cited

U.S. PATENT DOCUMENTS

| 2015/0259660 A1* | 9/2015 | Okuma ................ C12N 9/2437 435/99 |
| 2016/0053246 A1* | 2/2016 | Suda ..................... C12N 9/2437 435/91.21 |

FOREIGN PATENT DOCUMENTS

| CN | 101624597 A | 1/2010 |
| CN | 103409398 A | 11/2013 |
| JP | 64-063377 A | 3/1989 |
| JP | 2000-210081 A | 8/2000 |
| JP | 2004-065255 A | 3/2004 |
| JP | 2009-165399 A | 7/2009 |
| JP | 2012-196205 A | 10/2012 |
| WO | 00/39288 A1 | 7/2000 |
| WO | WO 2014155566 A1 * | 10/2014 ........... C12N 9/2437 |
| WO | WO 2014157492 A1 * | 10/2014 ........... C12N 9/2437 |

OTHER PUBLICATIONS

Banerjee et al., Improving enzymes for biomass conversion, Bioenerg. Res., 2010, 3, 82-92.*
Bornscheuer et al., Improved biocatalysts by directed evolution and rational protein design, Current Opinion Chem. Biol., 2001, 5, 137-43.*
Voget et al., Characterization of a metagenome-derived halotolerant cellulase, J. Biotechnol., 2006, 126, 26-36.*
Fontes et al., Possible roles for a non-modular, thermostable and proteinase-resistant cellulase from the mesophilic aerobic soil bacterium *Cellvibrio mixtus*, Appl. Microbiol. Biotechnol., 1997, 48, 473-79.*
GenBank, Accession No. AAB61461.1, 2000, www.ncbi.nlm.nih.gov.*
Kim et al., Characterization of a gene encoding cellulase from uncultured soil bacteria, FEMS Microbiol. Lett., 2008, 282, 41-51.*
Schmidt et al., Analysis of a marine picoplankton community by 16S rRNA gene cloning and sequencing, J. Bacteriol., 1991, 173, 4371-78.*
Uniprot, Accession No. A9AWC6, 2013, www.uniprot.org.*
Himmel et al., Current Opinion in Biotechnology, Aug. 1999, vol. 10, pp. 358-364.
Nakazawa et al., Directed evolution of endoglucanase 111 (Cell 2A) from Trichoderma reesei, Applied Microbiology and Biotechnology, 2009, vol. 83, pp. 649-657.
Heinzelman et al., A family of thermostable fungal cellulases created by structure-guided recombination, Proceedings of the National Academy of Sciences of the United States of America, 2009, vol. 106, pp. 5610-5615.
Zhang et al., Site-directed mutation of noncatalytic residues of Thermobifida fusca exocellulase Cel6B, European Journal of Biochemistry, 2000, vol. 267, pp. 3101-3115.
Wohlfahrt et al., Probing pH-Dependent Functional Elements in Proteins: Modification of Carboxylic Acid Pairs in Trichoderma reesei Cellobiohydrolase Cel6A, Biochemistry, 2003, vol. 42, pp. 10095-10103.

(Continued)

Primary Examiner — Robert B Mondesi
Assistant Examiner — Todd M Epstein
(74) Attorney, Agent, or Firm — Carrier Blackman & Associates, P.C.; Joseph P. Carrier; Fulchand P. Shende

(57) ABSTRACT

A method for selectively obtaining a natural variant of an enzyme having activity includes (1) a step of detecting an ORF sequence of a protein having enzyme activity from a genome database including base sequences of metagenomic DNA of environmental microbiota; (2) a step of obtaining at least one PCR clone including the ORF sequence having a full length, a partial sequence of the ORF sequence, or a base sequence encoding an amino acid sequence which is formed by deletion, substitution, or addition of at least one amino acid residue in an amino acid sequence encoded by the ORF sequence, by performing PCR cloning on at least one metagenomic DNA of the environmental microbiota by using a primer designed based on the ORF sequence; (3) a step of determining a base sequence and an amino acid sequence which is encoded by the base sequence for each PCR clone obtained in the step (2); and (4) a step of selecting a natural variant of an enzyme having activity by measuring enzyme activity of proteins encoded by each PCR clone obtained in the step (2).

3 Claims, 6 Drawing Sheets

(56) References Cited

OTHER PUBLICATIONS

Von Ossowski et al., Engineering the Exo-loop of Trichoderma reesei Cellobiohydrolase, Cel7A. A comparison with Phanerochaete chrysosporium Cel7D, Journal of Molecular Biology, 2003, vol. 333, pp. 817-829.
Kimura, Motoo, Evolutionary Rate at the Molecular Level, Nature Publishing Group, 1968, vol. 217(5129), pp. 624-626.
Quinlan et al., Pyrobayes: an improved base caller for SNP discovery in pyrosequences, Nature Methods, 2008, vol. 5, pp. 179-181.
Kanehisa, M., Science & Technology Japan, 1996, No. 59, pp. 34-38, http://www.genome.jp/kegg.
Hoff et al., Orphelia: predicting genes in metagenomic sequencing reads, Nucleic Acids Research, 2009, 37(Web Server issue: W101-W105).
Finn et al., The Pfam protein families database, Nucleic Acids Research Database, 2010, vol. 38, pp. D211-D222.
Durbin et al., 'The theory behind profile HMMs. Biological sequence analysis: probabilistic models of proteins and nucleic acids', 1998, Cambridge University Press.
Office Action dated Aug. 10, 2017 issued in the corresponding Chinese patent application 201510106938.6.
Science, Jan. 28, 2011, vol. 331, pp. 463-467.
Ishikawa et al., "Full-scale Research on Industrial Applicability of Super Thermostable Enzyme, How to use super themostable cellulase enzyme", AIAT Today, 2009, Jul. 2009, pp. 12 and 13, with partial English translation thereof.
Iqbal et al., "Biocatalysts and small molecule products from metagenomic studies", Current Opinion in Chemical Biology, 2012, vol. 16, pp. 109-116.
Schmeisser et al., "Metagenomics, biotechnology with non-culturable microbes", Appl. Microbiol Biotechnol, 2007, vol. 75, pp. 955-962.
Hong et al., "Cloning of a gene encoding thermostable cellobiohydrolase from Thermoascus aurantiacus and its expression in yeast", Appl. Microbiol Biotechnol, 2003, vol. 63, pp. 42-50.
del Castillo et al., "Isolation of Unselected Mutants of Alkaline Phosphatase in *Escherichia coli* Through Nitrosoguanidine Comutation and Comparison with Natural Variants", Biochemical Genetics, 1984, vol. 22, Nos. 5/6, pp. 467-482.
Office Action issued in the corresponding Japanese patent application 2014-050083 dated Sep. 12, 2017 and the English translation thereof.

* cited by examiner

FIG. 1

| | | | |
|---|---|---|---|
| AR19G-166QA | 1 | LDNPFIGAIGVNPDWATNVISQANQTADPTLAAQMRKVATYSTAVWLDRIAAITAGRGLERGHLDEALRQMQQAGQPVVI | 80 |
| AR19G-166QV | 1 | ............................................................................. | 80 |
| AR19G-166RA | 1 | ............................................................................. | 80 |
| AR19G-166RASFS | 1 | ............................................................................. | 80 |
| AR19G-166QA | 81 | TLVTYDLPNRDCSAAASNGELLVAQNGLARYKAEFIDPIVAILSDPRYAGLRIVTIIEPDSLPNLVTNLSIPACAEAQNA | 160 |
| AR19G-166QV | 81 | ............................................................................. | 160 |
| AR19G-166RA | 81 | ............................................................................. | 160 |
| AR19G-166RASFS | 81 | ..........................KQ................................................. | 160 |
| AR19G-166QA | 161 | YIEEGIRYAVNRLRTIPNVYIYLDIAHSGWLGWMNFNGAVNLYTQVVQGMDQGFNSIDGFITNVANYTPLEEPYLPDPNL | 240 |
| AR19G-166QV | 161 | ............................................................................. | 240 |
| AR19G-166RA | 161 | ............................................................................. | 240 |
| AR19G-166RASFS | 161 | ............................................................................. | 240 |
| AR19G-166QA | 241 | TIAGQPVRSASFYEWNPYFDELDYALALRNAFIGRGFPSTIGMLIDTSRNGWGGCSYGQCRPTGPSSDTSSVNAVDGSR | 320 |
| AR19G-166QV | 241 | ............................................................................. | 320 |
| AR19G-166RA | 241 | ............................................................................. | 320 |
| AR19G-166RASFS | 241 | ..............................................................R.............. | 320 |
| AR19G-166QA | 321 | VDRRYHRGNWCNQAGGIGERPQAAPRSGIDAYVWVKPPGESDGVSQPGIVDPDDPNKKFDPMCDPNGQSRYNSAYPTGAL | 400 |
| AR19G-166QV | 321 | ............................................................................. | 400 |
| AR19G-166RA | 321 | ............................................................................. | 400 |
| AR19G-166RASFS | 321 | ............................................................................. | 400 |
| AR19G-166QA | 401 | PNAPHAGRWFPQQFEILVRNAYPPIQP | 427 |
| AR19G-166QV | 401 | ........................... | 427 |
| AR19G-166RA | 401 | ........................... | 427 |
| AR19G-166RASFS | 401 | .......................S... | 427 |

Optimal temperature in PSA activity pH dependence in PSA activity

SEQUENCE LISTING

```
<160> NUMBER OF SEQ ID NOS: 11

<210> SEQ ID NO 1
<211> LENGTH: 427
<212> TYPE: PRT
<213> ORGANISM: Unknown
<220> FEATURE:
<223> OTHER INFORMATION: AR19G-166RASFS

<400> SEQUENCE: 1

Leu Asp Asn Pro Phe Ile Gly Ala Ile Gly Tyr Val Asn Pro Asp Trp
1               5                   10                  15
```

```
Ala Thr Asn Val Ile Ser Gln Ala Asn Gln Thr Ala Asp Pro Thr Leu
             20                  25                  30

Ala Ala Gln Met Arg Lys Val Ala Thr Tyr Ser Thr Ala Val Trp Leu
         35                  40                  45

Asp Arg Ile Ala Ala Ile Thr Ala Gly Arg Gly Leu Arg Gly His Leu
     50                  55                  60

Asp Glu Ala Leu Arg Gln Met Gln Gln Ala Gly Gln Pro Val Val Ile
 65                  70                  75                  80

Thr Leu Val Ile Tyr Asp Leu Ser Asn Arg Asp Cys Ser Ala Ala Ala
                 85                  90                  95

Ser Asn Gly Glu Leu Leu Val Ala Gln Asn Gly Leu Ala Arg Tyr Lys
             100                 105                 110

Ala Glu Phe Ile Asp Pro Ile Val Ala Ile Leu Ser Asp Pro Arg Tyr
         115                 120                 125

Ala Gly Leu Arg Ile Val Thr Ile Ile Glu Pro Asp Ser Leu Pro Asn
     130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                 165                 170                 175

Asn Val Tyr Ile Tyr Leu Asp Ile Ala His Ser Gly Trp Leu Gly Trp
             180                 185                 190

Asp Asn Asn Phe Asn Gly Ala Val Asn Leu Tyr Thr Gln Val Val Gln
         195                 200                 205

Gly Met Asp Gln Gly Phe Asn Ser Ile Asp Gly Phe Ile Thr Asn Val
     210                 215                 220

Ala Asn Tyr Thr Pro Phe Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                 245                 250                 255

Pro Tyr Phe Asp Glu Leu Asp Tyr Ala Leu Ala Leu Arg Asn Ala Phe
             260                 265                 270

Ile Gly Arg Gly Phe Pro Ser Thr Ile Gly Met Leu Ile Asp Thr Ser
         275                 280                 285

Arg Asn Gly Trp Gly Gly Cys Ser Tyr Gly Arg Cys Arg Pro Thr Gly
     290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                 325                 330                 335

Ile Gly Glu Arg Pro Gln Ala Ala Pro Arg Ser Gly Ile Asp Ala Tyr
         340                 345                 350

Val Trp Val Lys Pro Pro Gly Glu Ser Asp Gly Val Ser Gln Pro Gly
     355                 360                 365

Ile Val Asp Pro Asp Pro Asn Lys Lys Phe Asp Pro Met Cys Asp
370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Ser Glu Ile
             405                 410                 415

Leu Val Arg Asn Ala Tyr Pro Pro Ile Gln Pro
             420                 425
```

<210> SEQ ID NO 2
<211> LENGTH: 1284
<212> TYPE: DNA
<213> ORGANISM: Unknown
<220> FEATURE:
<223> OTHER INFORMATION: AR19G-166RASFS

<400> SEQUENCE: 2

| | | | | | |
|---|---|---|---|---|---|
| ttggacaatc | cattcatcgg | agccatcgga | tacgtgaatc | cggactgggc | aaccaatgtg | 60 |
| atcagccaag | cgaaccaaac | ggctgatcca | accttggcgg | ctcaaatgcg | taaggtggcc | 120 |
| acctactcca | cagctgtctg | gttggatcgt | atcgccgcca | tcaccgctgg | ccgcggattg | 180 |
| cgcgggcatt | tggatgaagc | gctacgccaa | atgcagcaag | ctggccagcc | ggttgtgatc | 240 |
| acccttgtga | tctatgatct | gtcaaatcga | gattgctctg | ctgctgcctc | caatggcgaa | 300 |
| ttactggtcg | cccagaatgg | actggcccgc | tacaaagcgg | agttcatcga | tcccatcgta | 360 |
| gccattctct | cagatccccg | atatgccggg | ctacgcatcg | tcaccatcat | cgaaccggac | 420 |
| tccttaccca | acctggtcac | gaacctcagc | atcccggcat | gcgcagaagc | tcagaatgca | 480 |
| tatatcgaag | ggatccgcta | tgcggtgaac | cggctgcgga | caattcccaa | cgtctacatc | 540 |
| tatctggata | tcgcccactc | aggctggttg | ggctgggata | taactttaa | tggggcagta | 600 |
| aatctctaca | cccaagttgt | gcaaggaatg | gatcaagggt | ttaacagtat | cgatggattc | 660 |
| atcaccaacg | ttgccaacta | tacccccttc | gaagaaccct | atttgcccga | tcccaacctg | 720 |
| accatcgctg | ggcaacccgt | tcgctctgcc | agcttctacg | aatggaaccc | ctactttgat | 780 |
| gagctggatt | acgctctggc | tctgcgcaac | gcttttatcg | acgaggctt | ccccagcacc | 840 |
| attgggatgc | tcatcgatac | cagccgaaac | gggtggggcg | gatgcagcta | tgggcgatgc | 900 |
| aggcccacgg | gtcccagttc | agataccagc | agcgtgaatg | cctacgtgga | cggctcgcga | 960 |
| gtagaccgac | gctatcatcg | gggcaactgg | tgtaaccagg | cgggtgggat | cggcgagcgc | 1020 |
| cctcaggccg | caccgcggtc | cggtatcgac | gcctacgtgt | gggtgaaacc | acctggggag | 1080 |
| tccgatgggg | tcagccaacc | cgggatcgtc | gatcccgacg | atcccaacaa | gaagttcgat | 1140 |
| cctatgtgtg | atcccaacgg | acagagccgg | tataactccg | catacccaac | tggggctctg | 1200 |
| cccaacgcgc | cccacgctgg | gcggtggttc | ccgcagcagt | ccgaaatcct | ggtgcggaac | 1260 |
| gcctatccgc | cgatccaacc | ctaa | | | | 1284 |

<210> SEQ ID NO 3
<211> LENGTH: 427
<212> TYPE: PRT
<213> ORGANISM: Unknown
<220> FEATURE:
<223> OTHER INFORMATION: AR19G-166QA

<400> SEQUENCE: 3

Leu Asp Asn Pro Phe Ile Gly Ala Ile Gly Tyr Val Asn Pro Asp Trp
 1               5                  10                  15

Ala Thr Asn Val Ile Ser Gln Ala Asn Gln Thr Ala Asp Pro Thr Leu
            20                  25                  30

Ala Ala Gln Met Arg Lys Val Ala Thr Tyr Ser Thr Ala Val Trp Leu
        35                  40                  45

Asp Arg Ile Ala Ala Ile Thr Ala Gly Arg Gly Leu Arg Gly His Leu
    50                  55                  60

Asp Glu Ala Leu Arg Gln Met Gln Gln Ala Gly Gln Pro Val Val Ile
65                  70                  75                  80

```
Thr Leu Val Ile Tyr Asp Leu Pro Asn Arg Asp Cys Ser Ala Ala Ala
                 85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
            115                 120                 125

Ala Gly Leu Arg Ile Val Thr Ile Ile Glu Pro Asp Ser Leu Pro Asn
130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
            195                 200                 205

Gly Met Asp Gln Gly Phe Asn Ser Ile Asp Gly Phe Ile Thr Asn Val
210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
            275                 280                 285

Arg Asn Gly Trp Gly Gly Cys Ser Tyr Gly Gln Cys Arg Pro Thr Gly
290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Ala Tyr
            340                 345                 350

Val Trp Val Lys Pro Pro Gly Glu Ser Asp Gly Val Ser Gln Pro Gly
            355                 360                 365

Ile Val Asp Pro Asp Pro Asn Lys Lys Phe Asp Pro Met Cys Asp
370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
            420                 425

<210> SEQ ID NO 4
<211> LENGTH: 1284
<212> TYPE: DNA
<213> ORGANISM: Unknown
<220> FEATURE:
<223> OTHER INFORMATION: AR19G-166QA

<400> SEQUENCE: 4
ttggacaatc cattcatcgg agccatcgga tacgtgaatc cggactgggc aaccaatgtg      60
atcagccaag cgaaccaaac ggctgatcca accttggcgg ctcaaatgcg taaggtggcc     120
```

```
acctactcca cagctgtctg gttggatcgt atcgccgcca tcaccgctgg ccgcggattg    180
cgcgggcatt tggatgaagc actacgccaa atgcagcaag ctggccagcc ggttgtgatc    240
acccttgtga tctatgatct gccaaatcga gattgctctg ctgctgcctc aatggcgaa     300 ttactggtcg cccagaatgg actggcccgc tacaaagcgg agttcatcga tcccatcgta    360
gccattctct cagatccccg atatgccggg ctacgcatcg tcaccatcat cgaaccggac    420
tccttaccca acctggtcac gaacctcagc atcccggcat gcgcagaagc tcagaatgca    480
tatatcgaag ggatccgcta tgcggtgaac cggctgcgga caattcccaa cgtctacatc    540
tatctggata tcgcccactc aggctggttg gctgggata taactttaa tggggcagta     600 aatctctaca cccaagttgt gcaaggaatg gatcaagggt taacagtat cgatggattc     660 atcaccaacg ttgccaacta tacccccctc gaagaaccct atttgcccga tcccaacctg    720
accatcgctg gcaacccgt tcgctctgcc agcttctacg aatggaaccc ctactttgat     780
gagctggatt acgctctggc tctgcgcaac gcttttatcg acgaggctt ccccagcacc     840 attgggatgc tcatcgatac cagccgaaac gggtggggcg gatgcagcta tgggcaatgc    900
aggcccacgg gtcccagttc agataccagc agcgtgaatg cctacgtgga cggctcgcga    960
gtagaccgac gctatcatcg gggcaactgg tgtaaccagg cgggtgggat cggcgagcgc   1020
cctcaggccg caccgcggtc cggtatcgac gcctacgtgt gggtgaaacc acctggggag   1080
tccgatgggg tcagccaacc cgggatcgtc gatcccgacg atcccaacaa gaagttcgat   1140
cctatgtgtg atcccaacgg acagagccgg tataactccg cataccaac tggggctctg    1200 cccaacgcgc ccacgctgg gcggtggttc ccgcagcagt tcgaaatcct ggtgcggaac    1260
gcctatccgc cgatccaacc ctaa                                          1284
```

<210> SEQ ID NO 5
<211> LENGTH: 474
<212> TYPE: PRT
<213> ORGANISM: Unknown
<220> FEATURE:
<223> OTHER INFORMATION: Amino acid sequence deduced from Open reading
      frame AR19G-166

<400> SEQUENCE: 5

```
Pro Thr Arg Thr Pro Thr Pro Ala Ala Pro Thr Ala Thr Pro Thr Pro
 1               5                  10                  15

Val Ala Pro Thr Ala Thr Pro Thr Arg Thr Pro Thr Pro Thr Leu Thr
                20                  25                  30

Ser Thr Pro Gly Pro Thr Pro Thr Pro Pro Ser Gly Thr His Leu
            35                  40                  45

Asp Asn Pro Phe Ile Gly Ala Ile Gly Tyr Val Asn Pro Asp Trp Ala
     50                  55                  60

Thr Asn Val Ile Ser Gln Ala Asn Gln Thr Ala Asp Pro Thr Leu Ala
 65                  70                  75                  80

Ala Gln Met Arg Lys Val Ala Thr Tyr Ser Thr Ala Val Trp Leu Asp
                85                  90                  95

Arg Ile Ala Ala Ile Thr Ala Gly Arg Gly Leu Arg Gly His Leu Asp
            100                 105                 110

Glu Ala Leu Arg Gln Met Gln Gln Ala Gly Gln Pro Val Val Ile Thr
        115                 120                 125

Leu Val Ile Tyr Asp Leu Pro Asn Arg Asp Cys Ser Ala Ala Ala Ser
    130                 135                 140
```

Asn Gly Glu Leu Leu Val Ala Gln Asn Gly Leu Ala Arg Tyr Lys Ala
145                 150                 155                 160

Glu Phe Ile Asp Pro Ile Val Ala Ile Leu Ser Asp Pro Arg Tyr Ala
            165                 170                 175

Gly Leu Arg Ile Val Thr Ile Ile Glu Pro Asp Ser Leu Pro Asn Leu
            180                 185                 190

Val Thr Asn Leu Ser Ile Pro Ala Cys Ala Glu Ala Gln Asn Ala Tyr
            195                 200                 205

Ile Glu Gly Ile Arg Tyr Ala Val Asn Arg Leu Arg Thr Ile Pro Asn
        210                 215                 220

Val Tyr Ile Tyr Leu Asp Ile Ala His Ser Gly Trp Leu Gly Trp Asp
225                 230                 235                 240

Asn Asn Phe Asn Gly Ala Val Asn Leu Tyr Thr Gln Val Val Gln Gly
            245                 250                 255

Met Asp Gln Gly Phe Asn Ser Ile Asp Gly Phe Ile Thr Asn Val Ala
            260                 265                 270

Asn Tyr Thr Pro Leu Glu Glu Pro Tyr Leu Pro Asp Pro Asn Leu Thr
            275                 280                 285

Ile Ala Gly Gln Pro Val Arg Ser Ala Ser Phe Tyr Glu Trp Asn Pro
        290                 295                 300

Tyr Phe Asp Glu Leu Asp Tyr Ala Leu Ala Leu Arg Asn Ala Phe Ile
305                 310                 315                 320

Gly Arg Gly Phe Pro Ser Thr Ile Gly Met Leu Ile Asp Thr Ser Arg
            325                 330                 335

Asn Gly Trp Gly Gly Cys Ser Tyr Gly Gln Cys Arg Pro Thr Gly Pro
            340                 345                 350

Ser Ser Asp Thr Ser Ser Val Asn Ala Tyr Val Asp Gly Ser Arg Val
            355                 360                 365

Asp Arg Arg Tyr His Arg Gly Asn Trp Cys Asn Gln Ala Gly Gly Ile
        370                 375                 380

Gly Glu Arg Pro Gln Ala Ala Pro Arg Ser Gly Ile Asp Ala Tyr Val
385                 390                 395                 400

Trp Val Lys Pro Pro Gly Glu Ser Asp Gly Val Ser Gln Pro Gly Ile
            405                 410                 415

Val Asp Pro Asp Asp Pro Asn Lys Lys Phe Asp Pro Met Cys Asp Pro
            420                 425                 430

Asn Gly Gln Ser Arg Tyr Asn Ser Ala Tyr Pro Thr Gly Ala Leu Pro
            435                 440                 445

Asn Ala Pro His Ala Gly Arg Trp Phe Pro Gln Gln Phe Glu Ile Leu
        450                 455                 460

Val Arg Asn Ala Tyr Pro Pro Ile Gln Pro
465                 470

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: 3' region
      of Forward primer

<400> SEQUENCE: 6
ttggacaatc cattcatcgg ag         22

<210> SEQ ID NO 7
<211> LENGTH: 29

-continued

```
<212> TYPE: DNA
<213> ORGANISM: Artificial Sequence
<220> FEATURE:
<223> OTHER INFORMATION: Description of Artificial Sequence: Forward
      primer

<400> SEQUENCE: 7
caccatgttg acaatccat tcatcggag                                    29

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Reverse
      primer

<400> SEQUENCE: 8
ttagggttgg atcggcggat ag                                          22

<210> SEQ ID NO 9
<211> LENGTH: 427
<212> TYPE: PRT
<213> ORGANISM: Unknown
<220> FEATURE:
<223> OTHER INFORMATION: AR19G-166QV

<400> SEQUENCE: 9
```

Leu Asp Asn Pro Phe Ile Gly Ala Ile Gly Tyr Val Asn Pro Asp Trp
 1               5                  10                  15

Ala Thr Asn Val Ile Ser Gln Ala Asn Gln Thr Ala Asp Pro Thr Leu
            20                  25                  30

Ala Ala Gln Met Arg Lys Val Ala Thr Tyr Ser Thr Ala Val Trp Leu
        35                  40                  45

Asp Arg Ile Ala Ala Ile Thr Ala Gly Arg Gly Leu Arg Gly His Leu
    50                  55                  60

Asp Glu Ala Leu Arg Gln Met Gln Gln Ala Gly Gln Pro Val Val Ile
65                  70                  75                  80

Thr Leu Val Ile Tyr Asp Leu Pro Asn Arg Asp Cys Ser Ala Ala Ala
                85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
    130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
        195                 200                 205

Gly Met Asp Gln Gly Phe Asn Ser Ile Asp Gly Phe Ile Thr Asn Val
    210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn

```
                    245                 250                 255
Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
        275                 280                 285

Arg Asn Gly Trp Gly Gly Cys Ser Tyr Gly Gln Cys Arg Pro Thr Gly
    290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Val Tyr
            340                 345                 350

Val Trp Val Lys Pro Pro Gly Glu Ser Asp Gly Val Ser Gln Pro Gly
        355                 360                 365

Ile Val Asp Pro Asp Asp Pro Asn Lys Lys Phe Asp Pro Met Cys Asp
    370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
            420                 425

<210> SEQ ID NO 10
<211> LENGTH: 427
<212> TYPE: PRT
<213> ORGANISM: Unknown
<220> FEATURE:
<223> OTHER INFORMATION: AR19G-166RA

<400> SEQUENCE: 10

Leu Asp Asn Pro Phe Ile Gly Ala Ile Gly Tyr Val Asn Pro Asp Trp
  1               5                  10                  15

Ala Thr Asn Val Ile Ser Gln Ala Asn Gln Thr Ala Asp Pro Thr Leu
             20                  25                  30

Ala Ala Gln Met Arg Lys Val Ala Thr Tyr Ser Thr Ala Val Trp Leu
         35                  40                  45

Asp Arg Ile Ala Ala Ile Thr Ala Gly Arg Gly Leu Arg Gly His Leu
     50                  55                  60

Asp Glu Ala Leu Arg Gln Met Gln Gln Ala Gly Gln Pro Val Val Ile
 65                  70                  75                  80

Thr Leu Val Ile Tyr Asp Leu Pro Asn Arg Asp Cys Ser Ala Ala Ala
                 85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
    130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
```

```
                    180                 185                 190
Asp Asn Asn Phe Asn Gly Ala Val Asn Leu Tyr Thr Gln Val Val Gln
                195                 200                 205

Gly Met Asp Gln Gly Phe Asn Ser Ile Asp Gly Phe Ile Thr Asn Val
            210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
                275                 280                 285

Arg Asn Gly Trp Gly Gly Cys Ser Tyr Gly Arg Cys Arg Pro Thr Gly
            290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Ala Tyr
            340                 345                 350

Val Trp Val Lys Pro Pro Gly Glu Ser Asp Gly Val Ser Gln Pro Gly
                355                 360                 365

Ile Val Asp Pro Asp Pro Asn Lys Lys Phe Asp Pro Met Cys Asp
370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
                420                 425

<210> SEQ ID NO 11
<211> LENGTH: 428
<212> TYPE: PRT
<213> ORGANISM: Herpetosiphon aurantiacus DSM 785
<220> FEATURE:
<223> OTHER INFORMATION: Catalytic domain of glycoside hydrolase
      family 6

<400> SEQUENCE: 11

Val Ala Asn Pro Phe Val Gly Ala Gln Gly Tyr Ile Asn Ser Glu Tyr
1               5                   10                  15

Ala Ala Arg Val Asn Ala Glu Ala Asn Ala Thr Gly Gly Thr Leu Gly
                20                  25                  30

Ser Gln Met Arg Gln Val Ala Ser Tyr Pro Thr Ala Val Trp Leu Asp
            35                  40                  45

Arg Ile Ala Ala Ile Ala Gly Ser Ser Glu Ser Met Gly Leu Arg Ala
        50                  55                  60

His Leu Asp Ala Ala Leu Val Gln Gln Gln Thr Ser Gly Gln Gln Val
65                  70                  75                  80

Ala Ile Ser Ile Val Val Tyr Asp Leu Pro Asn Arg Asp Cys Ala Ala
                85                  90                  95

Leu Ala Ser Asn Gly Glu Leu Lys Ile Ser Glu Asn Gly Leu Asn Arg
            100                 105                 110
```

```
Tyr Lys Thr Glu Tyr Ile Asp Pro Ile Ala Ala Ile Val Gly Glu Ser
        115                 120                 125
Lys Tyr Ala Ser Leu Arg Ile Val Val Ile Leu Glu Pro Asp Ser Leu
    130                 135                 140
Ser Asn Leu Val Thr Asn Ala Ser Ile Pro Ala Cys Ala Glu Ala Ile
145                     150                 155                 160
Ser Ser Gly Ala Tyr Val Gln Gly Val Gln Tyr Ala Ile Asn Lys Leu
                165                 170                 175
Asn Val Thr Ser Asn Val Tyr Ile Tyr Met Asp Ile Ala His Ser Gly
            180                 185                 190
Trp Leu Gly Trp Asp Ser Asn Phe Thr Pro Ala Ile Gln Leu Tyr Thr
        195                 200                 205
Gln Thr Val Arg Gly Thr Thr Lys Gly Leu Asn Gly Ile Asp Gly Phe
        210                 215                 220
Ile Ser Asn Thr Ala Asn Tyr Thr Pro Leu Asn Glu Val Phe Leu Pro
225                 230                 235                 240
Asn Ser Gly Leu Thr Leu Gly Gly Gly Asn Pro Ile Arg Ser Ser Leu
                245                 250                 255
Phe Tyr Glu Trp Asn Pro Tyr Phe Asp Glu Thr Asp Tyr Val Leu Ala
            260                 265                 270
Met Arg Asn Ala Phe Ile Thr Ala Gly Phe Pro Ser Gly Ile Gly Met
    275                 280                 285
Leu Ile Asp Thr Ser Arg Asn Gly Trp Gly Gly Thr Ala Arg Pro Thr
        290                 295                 300
Met Val Ser Ser Ser Asn Ser Leu Glu Ile Tyr Val Asn Asp Ser Lys
305                 310                 315                 320
Leu Asp Arg Arg Pro His Arg Gly Gly Trp Cys Asn Gln Ala Gly Ala
                325                 330                 335
Gly Ile Gly Glu Arg Pro Thr Ala Ala Pro Val Ser Gly Ile Asp Ala
                340                 345                 350
Tyr Val Trp Val Lys Pro Pro Gly Glu Ser Asp Gly Val Ala Thr Ala
            355                 360                 365
Gly Val Ile Asp Pro Thr Asp Pro Ala Lys Gln Phe Asp Ala Met Cys
370                 375                 380
Asp Pro Asn Ala Gln Asn Arg Tyr Asn Thr Ala Tyr Pro Thr Asn Ala
385                 390                 395                 400
Leu Ala Gly Ala Pro His Ala Gly Arg Trp Phe Pro Ser Gln Phe Ala
                405                 410                 415
Met Leu Val Arg Asn Ala Tyr Pro Pro Ile Ser Gln
                420                 425
```

METHOD FOR OBTAINING NATURAL VARIANT OF ENZYME AND SUPER THERMOSTABLE CELLOBIOHYDROLASE

BACKGROUND OF THE INVENTION

Field of the Invention

The present invention relates to a method for obtaining a natural variant of an enzyme and relates to super thermostable cellobiohydrolase obtained by the method.

Priority is claimed on Japanese Patent Application No. 2014-050083, filed on Mar. 13, 2014, the content of which is incorporated herein by reference.

Description of Related Art

Lignocellulose biomass is abundantly available on the earth, and for this reason, biofuel such as ethanol of which the raw material is lignocellulose is expected to become transportation energy replacing fossil fuels. For converting lignocellulose into ethanol, hydrolysis of cellulose or hemicelluloses needs to be performed. The cellulose hydrolysis is categorized into two methods including sulfuric acid hydrolysis and enzymatic hydrolysis. The enzymatic hydrolysis using glycoside hydrolases, which are collectively called cellulase enzymes in general, has advantages in that it does not generate sulfuric acid sludge unlike the sulfuric acid hydrolysis, consumes a small amount of energy, and results in high yield without causing excessive degradation of lignocellulose.

The cellulose constituting plant cell walls has a crystal structure in which the cellulose molecules are combined with each other through a strong hydrogen bond, and accordingly, the cellulose is practically not dissolved in water. Meanwhile, the enzymatic hydrolysis of cellulose is a solid-liquid reaction. During the solid-liquid reaction, the hydrolysis of the crystalline cellulose occurs on the solid surface, and consequentially, hydrolysis efficiency resulting from the enzyme is markedly low. For instance, cellobiohydrolase (CBH) as a main cellulose hydrolase results in a hydrolysis rate that is lower than that of other polysaccharide lyases by a single digit or double digits. Accordingly, the enzyme needs to be used in a large amount for hydrolysis of cellulose biomass, and this is a main factor causing a rise in the cost of cellulose-based biofuels. In order to reduce the cost of cellulose ethanol, the hydrolysis efficiency of the cellulase enzyme needs to be greatly improved.

As one of the methods for improving the enzyme efficiency, thermostability of the enzyme protein is improved. In order to improve the thermostability of the enzyme protein, various means for reengineering the enzyme by introduction of amino acid mutation, such as a directed evolution (DE) method in which amino acid sequences are randomly substituted, a site-directed mutagenesis (SDM) method in which amino acid substitution is performed only in a specific site, and a method in which a chimeric sequence is formed by cleaving a plurality of genes at several sites and then shuffling the fragments, have been tried.

Theoretically, the enzyme modification performed by the DE method has poor efficiency. This is because a so-called problem of "combinatorial explosion" occurs in which the number of variants increases exponentially as the number of the cases of point mutation increases. In order to obtain optimal amino acid sequences, it is necessary to construct mutant libraries for combinations of all amino acid residues and to perform a functional amino assay, however, this is impossible in principle. Furthermore, while most of the mutations are loss-of-function type mutation resulting in loss of function, neutral mutation or gain-of-function type mutation by which advantageous functions are obtained is extremely rare, and also hinders the DE method from efficiently searching for optimal amino acid sequences.

Because an enormous number of mutant libraries should be screened to obtain effective mutants, and there is no effective high-throughput screening method or a stable gene expression system (for example, see Himmel et al., Current Opinion in Biotechnology, 1999, vol. 10, p. 358~364.), the function of the cellulase enzyme has not been sufficiently improved by the DE method.

For example, Nakazawa et al. reported that they reengineered endoglucanase EGIII of a wood-rotting fungus, *Trichoderma reesei*, by the DE method (see Nakazawa et al., Applied Microbiology and Biotechnology, 2009, vol. 83, p. 649~657). The EGIII is a protein which is constituted with 218 amino acid residues and has a relatively small molecular weight. However, even in the case of such a small size protein, the number of variants obtained by introducing mutation causing amino acid substitution into any single site becomes 4,360 (20×218); the number of variants obtained by introducing mutation into any two sites becomes 9,460,000 (20×20×218×217÷2); and the number of variants obtained by introducing mutation into any three sites becomes 13,624,130,000 (20×20×20×(218×217×216÷6)) due to the combinatorial explosion.

In order to obtain variants in which mutation has occurred in only two to three sites, tens of millions to tens of billions of mutant libraries need to be constructed, and functional screening thereof needs to be performed. Therefore, this method is not practical. Although Nakazawa et al. performed functional screening for a total of 11,000 first- and second-generation mutants, the optimal temperature thereof was increased by only +5° C., and they did not achieve great improvement in thermostability. Naturally, if the scale of the mutant library is small, effective mutants are not discovered. Moreover, from 9,000 colonies of the mutant libraries of the first generation having undergone the functional screening, the variants having CMC hydrolytic activity are obtained in only 46 colonies. The remaining 8,954 mutants are considered to have lost their function due to amino acid mutation or have gene expression failure, and most of the random mutations caused by erroneous PCR of the DE method result in the loss of function of the enzyme protein. In this way, because the DE method produces a large amount of loss-of-function type mutants, the screening efficiency thereof is extremely poor.

The gene shuffling method has not succeeded in obtaining chimeric genes having thermostability higher than that of parental genes thereof. For example, Heinzelman et al. proposed a method for improving the function of an enzyme by creating chimeric genes by means of cleaving a plurality of cellobiohydrolase genes at several sites and shuffling the fragments thereof (see Heinzelman et al., Proceedings of the National Academy of Sciences of the United States of America, 2009, vol. 106, p. 5610~5615). According to this method, in order to improve the thermostability of an exoglucanase CBH II of *Trichoderma reesei*, genes of the enzyme CBH II of thermophilic filamentous fungi *Humicola insolens* and *Chaetomium thermophilum* are combined together by gene shuffling, thereby preparing a chimeric enzyme. However, the thermostability of the chimeric enzyme is not higher than that of CBH II of the thermophilic filamentous fungus *Chaetomium thermophilum* as a parent thereof and the gene shuffling is ineffective.

While the DE method is a method for causing amino acid substitution by random mutation, the SDM method is a method for causing mutation such as substitution, deletion, or insertion of amino acids based on the three-dimensional structure data of enzyme proteins. Unlike the DE method, the SDM method does not require screening of an enormous number of mutants. However, generally, it is difficult to identify the site involved in the improvement of the function of an enzyme, and it is rare for the SDM method to exert a marked effect on the improvement of the cellulase enzyme.

For example, in cellobiohydrolase, the N terminal and C terminal thereof have a loop structure and form a tunnel structure covering the active center. Based on such a structure, the SDM method for substituting the amino acid inside the loop has been tried. In order to improve the thermostability, Zhang et al. estimated the three-dimensional structure of a cellobiohydrolase TfCel6B of a thermophilic actinomycete *Thermobifida fusca*, and introduced a disulfide bond into the loop of the N terminal and the C terminal forming the tunnel structure of the active site by double mutation. However, contrary to their expectation, in the obtained variant, a temperature $T_{50}$ at which the enzymatic activity halves was reduced by 10° C. (see Zhang et al., European Journal of Biochemistry, 2000, vol. 267, p. 3101~3115). Zhang at al. reported that although they substituted glycine residues at 4 sites with alanine, serine, and proline, no cellubiohydrolase of which the thermostability was improved by mutation was obtained, and the thermostability was reduced by 5° C. to 10° C. in most of the mutants.

Furthermore, Wohlfahrt et al. reported that in order to improve heat stability of a cellubiohydrolase TrCel6A belonging to a GH6 family of the filamentous fungus *T. reesei*, they manufactured a variant by introducing mutation into amino acid residues positioned on the N terminal loop and the C terminal loop and amino acids residues positioned in the near of the loops, and as a result, a thermal denaturation temperature (Tm) of the variant increased at a pH of 7.0, but the Tm value decreased at a pH of 5.0 which is the optimal pH of wild type TrCel6A (see Wohlfahrt et al., Biochemistry, 2003, vol. 42, p. 10095~10103). Meanwhile, in order to stabilize an exo-loop structure forming a tunnel loop of the active center of a cellubiohydrolase TrCel7A belonging to a GH7 family of the filamentous fungus *T. reesei*, von Ossowski et al. prepared a variant obtained by introducing an SS (disulfide) bond into the loop, but in this variant, the improvement of the thermostability was not observed at all (see von Ossowski et al., Journal of Molecular Biology, 2003, vol. 333, p. 817~829). As described above, the attempt at introducing a hydrogen bond or an SS bond into the C terminal loop forming the loop structure, which is considered to be deeply involved with the function of the cellobiohydrolase enzyme, has been made in various ways, but up to now, the attempt has not yet led to success in improvement of the function of the enzyme, such as the improvement of thermostability.

From the comparison between homologous genes of species, it has been found that there is a domain which is well preserved and a domain into which amino acid mutation is frequently introduced. The preserved domain is called a "consensus sequence" because it is a common sequence that characterizes a protein of a specific category. If amino acid residues in the consensus sequence are mutated, the enzyme easily loses its function. It is considered that for this reason, the site has been well preserved through a long evolutionary process. Accordingly, the mutation that causes amino acid mutation in the consensus sequence is highly likely to result in loss of function. Therefore, the SDM method has been tried which causes mutation in a protein except for the consensus sequence. However, this method can only be applied to enzymes of which the three-dimensional structure of protein is determined by X-ray crystal structure analysis, and there are only a few enzyme proteins of which the three dimensional structure has been identified.

SUMMARY OF THE INVENTION

An object of the present invention is to provide a method for efficiently obtaining a gain-of-function type variant.

Another object of the present invention is to provide a novel super thermostable cellobiohydrolase that is obtained by the aforementioned method, a polynucleotide that encodes the super thermostable cellobiohydrolase, an expression vector that is for expressing the super thermostable cellobiohydrolase, a transformant into which the expression vector has been incorporated, and a method for manufacturing a cellulose degradation product using the super thermostable cellobiohydrolase.

In order to achieve the above objects, the present inventors performed extensive research. As a result, they found that if colony PCR is performed for a large number of colonies of metagenomic DNA of microbiota contained in altithermal soil, for example, 300 or less colonies of metagenomic DNA of microbiota contained in altithermal soil by using a primer which is designed from a base sequence of a cellobiohydrolase enzyme separated from the metagenomic DNA of the microbiota contained in altithermal soil, it is possible to obtain a natural variant which causes substitution of a plurality of amino acids or has activities of a plurality of super thermostable cellobiohydrolases having silent single nucleotide polymorphism (SNP). Based on the finding, the present inventors completed the present invention.

In the present invention, the term "natural variant" refers to a mutant that is naturally generated (that is, incidentally generated) instead of being generated by artificial means.

The term "super thermostable" means that an optimum temperature of an enzyme activity or a thermal denaturation temperature of an enzyme protein is 80° C. or greater.

That is, a method for obtaining a natural variant of an enzyme, a method for manufacturing a variant of an enzyme, a super thermostable cellobiohydrolase, a polynucleotide that encodes the super thermostable cellobiohydrolase, an expression vector that is for expressing the super thermostable cellobiohydrolase, a transformant into which the expression vector has been incorporated, a method for manufacturing a super thermostable cellobiohydrolase, a cellulase mixture, and a method for manufacturing a cellulose degradation product of the present invention are exemplified in the following [1] to [13].

[1] A method for selectively obtaining a natural variant of an enzyme having activity, including:

(1) a step of detecting an ORF (hereinafter, also referred to as an "open reading frame" in some cases) sequence of a protein having enzyme activity from a genome database including base sequences of metagenomic DNA of environmental microbiota;

(2) a step of obtaining at least one PCR clone including the ORF sequence having a full length, a partial sequence of the ORF sequence, or a base sequence encoding an amino acid sequence which is formed by deletion, substitution, or addition of at least one amino acid residue in an amino acid sequence encoded by the ORF sequence, by performing PCR cloning on at least one metagenomic DNA of the environmental microbiota by using a primer designed based on the ORF sequence;

(3) a step of determining a base sequence and an amino acid sequence which is encoded by the base sequence for each PCR clone obtained in the step (2); and (4) a step of selecting a natural variant of an enzyme having activity by measuring enzyme activity of proteins encoded by each PCR clone obtained in the step (2).

[2] A method for manufacturing a variant of an enzyme having activity, including:

(1) a step of detecting an ORF sequence of a protein having enzyme activity from a genome database including base sequences of metagenomic DNA of environmental microbiota;

(2) a step of obtaining at least one PCR clone including the ORF sequence having a full length, a partial sequence of the ORF sequence, or a base sequence encoding an amino acid sequence which is formed by deletion, substitution, or addition of at least one amino acid residue in an amino acid sequence encoded by the ORF sequence, by performing PCR cloning on at least one metagenomic DNA of the environmental microbiota by using a primer designed based on the ORF sequence:

(3) a step of determining a base sequence and an amino acid sequence which is encoded by the base sequence for each PCR clone obtained in the step (2);

(4) a step of measuring enzyme activity of proteins encoded by each PCR clone obtained in the step (2);

(5) a step of investigating the relationship between the amino acid sequence encoded by the ORF sequence and the enzyme activity after the steps (3) and (4); and (6) a step of manufacturing a variant improved in terms of the enzyme activity by causing deletion, substitution, or addition of at least one amino acid residue in the amino acid sequence encoded by the ORF sequence, based on the relationship between the amino acid sequence and the enzyme activity that is obtained in the step (5).

[3] The method for manufacturing a variant of an enzyme described in [2], in which the metagenomic DNA of the environmental microbiota is metagenomic DNA derived from altithermal soil, and the enzyme is a thermostable enzyme that exhibits enzyme activity at a temperature of at least 70° C.

[4] The method for manufacturing a variant of an enzyme described in [2] or [3], in which the enzyme is cellulase.

[5] A super thermostable cellobiohydrolase having a cellobiohydrolase catalyst domain including (A) a polypeptide that consists of an amino acid sequence represented by SEQ ID NO:1, (B) a polypeptide that consists of an amino acid sequence formed by deletion, substitution, or addition of at least one amino acid residue in the amino acid sequence represented by SEQ ID NO: 1 (here, serine in the $88^{th}$ position, phenylalanine in the $230^{th}$ position, and serine in the $414^{th}$ position in the amino acid sequence, in which the deletion, substitution, or addition of the amino acid has not yet occurred, are excluded) and has cellobiohydrolase activity under conditions of at least a temperature of 80° C. and a pH of 5.5, or (C) a polypeptide that consists of an amino acid sequence (here, in the amino acid sequence, the $88^{th}$ position is serine, the $230^{th}$ position is phenylalanine, and the $414^{th}$ position is serine) having sequence identity of equal to or higher than 80% with the amino acid sequence represented by SEQ ID NO: 1 and has cellobiohydrolase activity under conditions of at least a temperature of 80° C. and a pH of 5.5.

[6] A polynucleotide having a domain encoding a cellobiohydrolase catalyst domain including (a) a base sequence encoding a polypeptide that consists of an amino acid sequence represented by SEQ ID NO:1, (b) a base sequence encoding a polypeptide that consists of an amino acid sequence formed by deletion, substitution, or addition of at least one amino acid residue of the amino acid sequence represented by SEQ ID NO:1 (here, serine in the $88^{th}$ position, phenylalanine in the $230^{th}$ position, and serine in the $414^{th}$ position in the amino acid sequence, in which the deletion, substitution, or addition of the amino acid has not yet occurred, are excluded) and has cellobiohydrolase activity under conditions of at least a temperature of 80° C. and a pH of 5.5, (c) a base sequence encoding a polypeptide that consists of an amino acid sequence (herein, in the amino acid sequence, the $88^{th}$ position is serine, the $230^{th}$ position is phenylalanine, and the $414^{th}$ position is serine) having sequence identify of equal to or higher than 80% with the amino acid sequence represented by SEQ ID NO:1 and has cellobiohydrolase activity under conditions of at least a temperature of 80° C. and a pH of 5.5, (d) a base sequence encoding a polypeptide that have sequence identity of equal to or higher than 80% with an amino acid sequence represented by SEQ ID NO:2 and has cellobiohydrolase activity under conditions of at least a temperature of 80° C. and a pH of 5.5, or (e) a base sequence encoding a polypeptide that is a base sequence of a polynucleotide hybridized with a polynucleotide consisting of the base sequence represented by SEQ ID NO:2 under stringent conditions and has cellobiohydrolase activity under conditions of at least a temperature of 80° C. and a pH of 5.5.

[7] An expression vector into which the polynucleotide described in [6] has been incorporated and which can express a polypeptide having cellobiohydrolase activity under conditions of at least a temperature of 80° C. and a pH of 5.5 in a host cell.

[8] A transformant into which the expression vector described in [7] has been introduced.

[9] The transformant described in [8] that is a eukaryotic microorganism.

[10] A method for manufacturing a super thermostable cellobiohydrolase, including a step of producing a super thermostable cellobiohydrolase in the transformant described in [8] or [9].

[11] A cellulase mixture containing the super thermostable cellobiohydrolase described in [5] or the super thermostable cellobiohydrolase manufactured by the method for manufacturing a super thermostable cellobiohydrolase described in [10] and at least one other kind of cellulase.

[12] A method for manufacturing a cellulose degradation product, including a step of producing a cellulose degradation product by bringing a cellulose-containing material into contact with the super thermostable cellobiohydrolase described in [5], the transformant described in [8] or [9], or the super thermostable cellobiohydrolase manufactured by the method for manufacturing a super thermostable cellobiohydrolase described in [10].

[13] The method for manufacturing a cellulose degradation product described in [12], further including a step of bringing the cellulose-containing material into contact with at least one other kind of cellulase.

By using the method for obtaining a natural variant of an enzyme according to the present invention and the method for manufacturing a variant of an enzyme utilizing the aforementioned method, it is possible to efficiently obtain a gain-of-function type variant of an enzyme.

Furthermore, the super thermostable cellobiohydrolase according to the present invention has cellobiohydrolase activity under conditions of at least a temperature of 80° C. and a pH of 5.5. Therefore, the super thermostable cellobiohydrolase is suitable for the hydrolysis of cellulose under high-temperature conditions.

Moreover, the polynucleotide according to the present invention, the expression vector into which the polynucleotide has been incorporated, and the transformant into which the expression vector has been introduced are suitably used for manufacturing the super thermostable cellobiohydrolase according to the present invention.

BRIEF DESCRIPTION OF THE DRAWINGS

FIG. 1 is a view showing the alignment of the amino acid sequences of AR19G-166RA, AR19G-166QV, AR19G-166QA, and AR19G-166RASFS in Example 1.

DETAILED DESCRIPTION OF THE INVENTION

Figure 2:
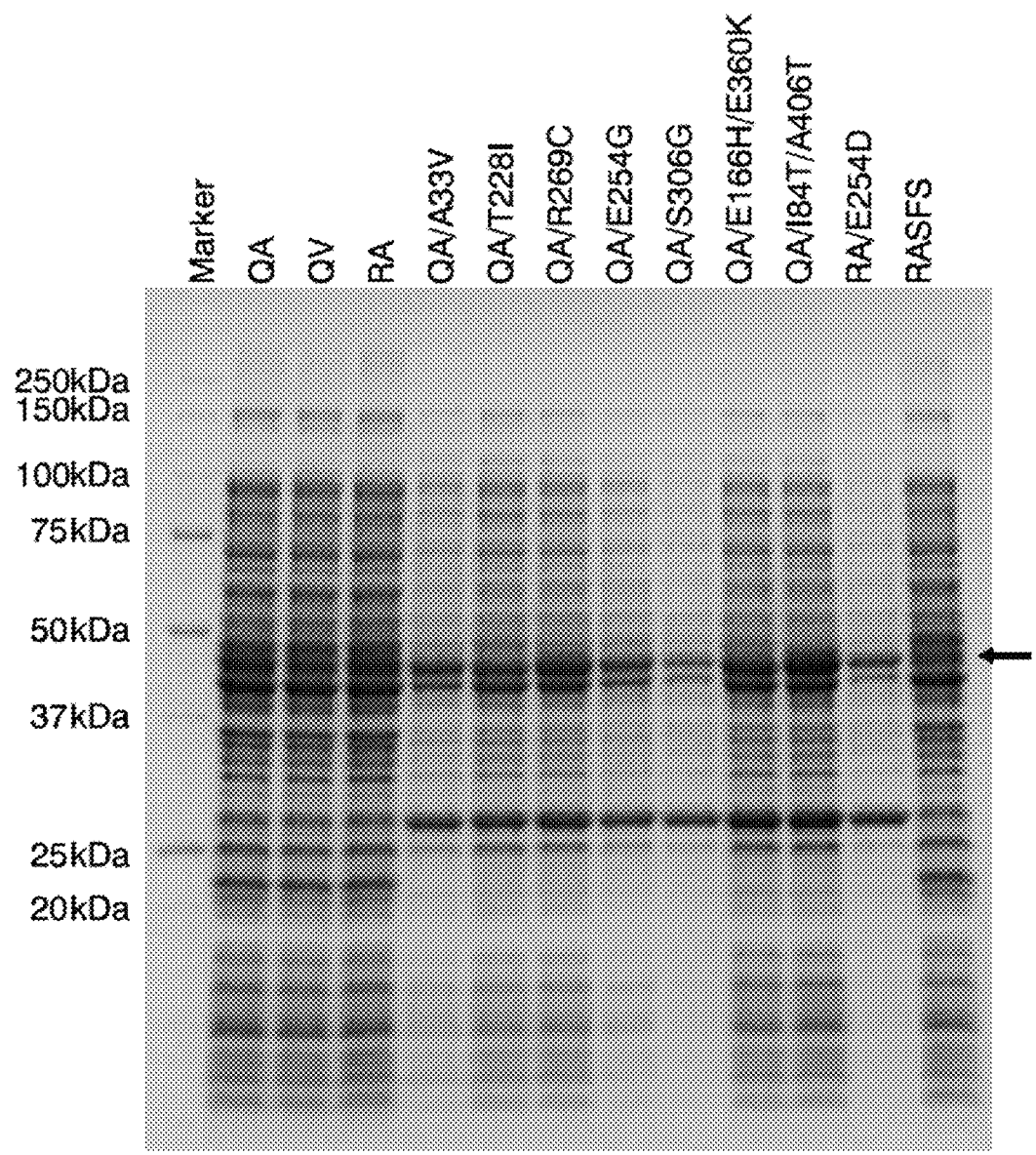
FIG. 2 is a view showing results of SDS-PAGE analysis performed in Example 1 on cellobiohydrolase enzyme proteins encoded by natural variants of the AR19G-166 gene.

[Method for Obtaining Natural Variant of Enzyme]

The method for selectively obtaining a natural variant of an enzyme having activity according to the present invention (hereinafter, referred to as a "natural variant obtaining method according to the present invention" in some cases) relates to a method for selectively obtaining a natural variant of an enzyme having activity from metagenomic DNA prepared from an environmental microbiota, by using a primer designed based on an open reading frame (ORF) sequence of the enzyme gene.

The metagenomic DNA can be prepared from the environmental microbiota by a known method using, for example, a DNA extraction kit (ISOIL Large for Beads ver. 2, NIPPON GENE CO., LTD.).

If a variant library can be constructed by collecting only gain-of-function type mutants, it is possible to avoid useless screening performed for removing the enormous number of dysfunctional mutants generated, and to efficiently obtain variants having improved functions by performing a functional assay on a relatively small number of amino acid substitution variants. The metagenomic DNA prepared from the environmental microbiota includes a large amount of gain-of-function type natural variants. Therefore, if the metagenomic DNA is used as a base, it is possible to efficiently obtain gain-of-function type variants.

In the present invention, the term "having activity" means that there is a significant difference in the amount of reducing-end or a chromogenic reaction, with respect to at least one substrate as compared to the negative control.

The reason why the metagenomic DNA prepared from the environmental microbiota includes a large amount of gain-of-function type natural variants can be explained based on the neutral theory of molecular evolution. Single nucleotide polymorphism (SNP) is one of the base sequence polymorphisms frequently occurring in genomic DNA. For example, it is said that in human genomic DNA. SNP occurs approximately in one base per about 1,000 bases. The SNP occurring in genes causes amino acid mutation or causes silent mutation that does not entail amino acid mutation, such as synonymous substitution or SNP on an intron. When the SNP causes amino acid mutation, proteins encoded by the gene undergo some structural or functional change in some cases. According to the neutral theory of molecular evolution that is widely accepted (Kimura, Nature, 1968, vol. 217 (5129), p. 624~626), genetic mutation causing amino acid substitution, which may exert a negative influence on the survival value of individuals by causing functional deterioration or functional failure and thus is evolutionarily disadvantageous, is excluded from a group. In contrast, if mutation is evolutionarily neutral or advantageous, an individual carrying the mutant gene is not excluded from the group. The gene is passed down to the next generation, and genetic diversity such as SNP is accumulated. According to the neutral theory of molecular evolution, the natural variant having the SNP causing amino acid substitution is considered to include neutral or advantageous mutation that does not cause functional failure, that is, gain-of-function type mutation.

That is, the natural variant obtaining method according to the present invention is a method for selectively obtaining a natural variant of an enzyme having activity, and includes the following steps (1) to (4).

(1) A step of detecting an ORF sequence of a protein having enzyme activity from a genome database including base sequences of metagenomic DNA of environmental microbiota (2) A step of obtaining at least one PCR clone including the ORF sequence having a full length, a partial sequence of the ORF sequence, or a base sequence encoding an amino acid sequence which is formed by deletion, substitution, or addition of at least one amino acid in an amino acid sequence encoded by the ORF sequence, by performing PCR cloning on at least one metagenomic DNA of the environmental microbiota by using a primer designed based on the ORF sequence (3) A step of determining a base sequence and an amino acid sequence which is encoded by the base sequence for each PCR clone obtained in the step (2)

(4) A step of selecting a natural variant of an enzyme having activity by measuring enzyme activity of proteins encoded by each PCR clone obtained in the step (2)

The metagenomic DNA of the environmental microbiota is obtained by physically fragmenting genomic DNA of environmental microbiota (a group of microorganisms contained in an environmental sample) into small pieces. As the metagenomic DNA of the environmental microbiota used in the present invention, it is possible to use metagenomic DNA prepared from microbiota of soil, sludge, lakewater, seawater, and the like. In order to obtain an enzyme variant excellent in thermostability, it is preferable to use metagenomic DNA prepared from microbiota of a sample collected from an altithermal environment. Examples of the sample collected from an altithermal environment include a sample of soil of high temperature hot spring and the like.

Herein, examples of the "soil of high temperature hot spring" include hot spring water and the like containing soil, mud, and biomass of 30° C. to 80° C., and the like.

In the method for obtaining a natural variant having activity according to the present invention, first, as the step (1), an ORF sequence of a protein having enzyme activity is detected from a genomic database including base sequences of metagenomic DNA of environmental microbiota. The genomic database can be created by performing a method such as a shotgun sequencing method used for sequence analysis of long-chain DNA on the metagenomic DNA of the environmental microbiota.

Specifically, the metagenomic DNA of the environmental microbiota is subjected to assembly and annotation of shotgun sequencing data, and an ORF sequence encoding a specific amino acid sequence is detected. The ORF sequence of a protein having target enzyme activity can be detected by a known technique such as homology (sequence identity) analysis of base sequence based on a base sequence of a gene which has the target enzyme activity and of which the base sequence is already known. For example, the homology analysis is preferably set so as to detect a sequence 30% or more homologous to the base sequence of a gene which has the enzyme activity and of which the base sequence is already known.

Thereafter, as the step (2), by using a primer designed based on the ORF sequence, PCR cloning is performed on at least one metagenomic DNA of the environmental microbiota. The primer to be used is preferably a primer which is designed so as to be able to amplify at least a domain including a catalyst domain of the enzyme in the ORF sequence by PCR. By performing PCR cloning from the metagenomic DNA, at least one PCR clone, which consists of a base sequence encoding an amino acid sequence formed by deletion, substitution, or addition of at least one amino acid residue in the ORF sequence having a full length; a partial sequence of the ORF sequence; or an amino acid sequence encoded by the ORF sequence, is cloned.

Then the base sequence of each PCR clone obtained in the step (2) is analyzed, and an amino acid sequence encoded by the PCR clone is determined (step (3)). Subsequently, a protein encoded by the PCR clone is manufactured, the enzyme activity of the protein is measured, and a variant of an enzyme having activity is selected (step (4)). In this way, a variant having enzyme activity can be selectively obtained.

In the present invention, it is preferable to perform PCR cloning on a plurality of metagenomic DNAs derived from different sources by using the same primer. If PCR cloning is performed not only on the metagenomic DNA as a base for designing the primer but also on a plurality of metagenomic DNAs derived from different sources, and a PCR library is constructed by collecting colonies combined with a plasmid containing amplified fragments of the designed primer on a large scale, for example, by collecting hundreds or more colonies, more amino acid substitution variants (natural variants) of the enzyme gene are obtained.

Generally, in PCR cloning, target genes are cloned by collecting 1 to 10 colonies. However, in the natural variant obtaining method according to the present invention, it is preferable to clone genes by collecting colonies in a large number, such as 100 at least, per each metagenomic DNA sample. In this way, it is possible to construct a library constituted with natural variants including various SNPs of the target enzyme genes.

[Method for Manufacturing Variant of Enzyme]

In the present invention, the natural variant library constructed as above is subjected to functional screening, and in this way, the function of the enzyme, such as thermostability, is efficiently improved. As a result, it is possible to efficiently manufacture a novel variant improved in terms of the enzyme activity.

That is, the method for manufacturing a variant of an enzyme according to the present invention (hereinafter, the method will be referred to as a "variant manufacturing method according to the present invention" in some cases) further includes the following steps (5) and (6) in addition to the steps (1) to (4).

(5) A step of investigating the relationship between the amino acid sequence encoded by the ORF sequence and the enzyme activity for a plurality of variants alter the steps (3) and (4)

(6) A step of manufacturing a variant improved in terms of the enzyme activity by causing deletion, substitution, or addition of at least one amino acid residue in the amino acid sequence encoded by the ORF sequence, based on the relationship between the amino acid sequence and the enzyme activity that is obtained in the step (5).

Herein, the term "improvement of enzyme activity" means that the activity of the enzyme encoded by the ORF sequence, in which deletion, substitution, or addition of at least one amino acid residue has occurred, is higher than the activity of the enzyme encoded by the ORF sequence in which deletion, substitution, or addition of the amino acid residue has not yet occurred.

For example, in the step (5), if enzyme activities of proteins, which are encoded by two PCR clones differing from each other in terms of one, two, or more amino acid residues in the amino acid sequence, are compared with each other, amino acid mutation that can improve the enzyme activity is clearly seen. Subsequently, in the step (6), if base mutation for causing amino acid mutation that can further improve the enzyme activity is introduced into either the DNA fragments consisting of the ORF sequence or the PCR clone obtained in the step (2), and thus at least one amino acid residue in the amino acid sequence encoded by the ORF sequence undergoes deletion, substitution, or addition, a variant improved in terms of the enzyme activity is manufactured. The substitution or the like of the base that is for causing mutation of one, two, or more amino acid residues can be performed by a common method.

[Super Thermostable Cellobiohydrolase]

As shown in Example 1, which will be described later, the present inventors prepared genomic DNA (metagenomic DNA) of a group of microorganisms from soil of high temperature hot spring (for example, hot spring water and the like containing soil, mud, and biofilm of 30° C. to 80° C.) collected from five sites in one place in Japan. Using the respective metagenomic DNAs, the present inventors performed the natural variant obtaining method according to the present invention and obtained a novel cellobiohydrolase excellent in thermostability.

Specifically, first, from one metagenomic DNA, thirteen open reading frames (ORF) having a high degree of amino acid sequence homology (that is, identity of equal to or higher than 30%) with a known cellobiohydrolase (CBH) enzyme were obtained. Based on base sequence information of these ORFs, a primer was designed, and by PCR, the cellobiohydrolase catalyst domain was cloned from the metagenomic DNA of the soil of the high temperature hot spring. The DNA cloned by PCR (PCR clone) was incorporated into *E. coli* such that a protein encoded by the base sequence was expressed, and functional screening was performed by assay for phosphoric acid-swollen Avicel (PSA) degradation activity and carboxymethyl cellulose (CMC) degradation activity.

Finally, from one open reading frame AR19G-166, a novel super thermostable cellobiohydrolase (AR19G-166RA) having PSA degradation activity was obtained.

The open reading frame AR19G-166 had an incomplete sequence in which methionine of the start codon was lost. Accordingly, the AR19G-166RA gene cloned from the ORF was a partial gene constituted only with a GH6 catalyst domain.

Thereafter, by using a primer designed based on the ORF sequence, five metagenomic DNAs were cloned by PCR cloning. As a result, twelve kinds of amino acid substitution variants of AR19G-166RA were finally obtained. The super thermostable cellobiohydrolase according to the present invention is AR19G-166RASFS (a variant in which the amino acid residue in the $299^{th}$ position is arginine, the amino acid residue in the $351^{st}$ position is alanine, the amino acid residue in the $88^{th}$ position is serine, the amino acid residue in the $230^{th}$ position is phenylalanine, and the amino acid residue in the $414^{th}$ position is serine) having the highest thermostability among the variants of AR19G-166RA. The amino acid sequence of AR19G-166QA that most frequently appeared is represented by SEQ ID NO:3, and a base sequence encoding the amino acid sequence is represented by SEQ ID NO:4. The amino acid sequence of AR19G-166RASFS is represented by SEQ ID NO:1, and a base sequence encoding the amino acid sequence is represented by SEQ ID NO:2.

As shown in Example 1, which will be described later, AR19G-166RASFS exhibited a high degree of hydrolytic activity with respect to PSA. Moreover, the AR19G-166RASFS exhibited degradation activity with respect to Lichenan consisting of glucan having a β-1,3 bond and a β-1,4 bond or to Avicel as crystalline cellulose, though the degradation activity was weak. In contrast, the AR19G-166RASFS exhibited almost no degradation activity with respect to CMC or to Laminarin consisting of glucan having a β-1,3 bond and a β-1,6 bond. Moreover, as a result of searching for the amino acid sequence of the AR19G-166RASFS in a known amino acid sequence database, it was confirmed that an amino acid sequence having the highest sequence identity with the aforementioned amino acid sequence is a glucoside hydrolase (SEQ ID NO: 11) belonging to a GH6 family of *Herpetosiphon aurantiacus* DSM 785 as a known mesophilic thermophilic bacterium in the phylum Chlroflexi, and the sequence identity was only 66%. The substrate specificity. HPLC analysis of the product of a hydrolysis reaction of PSA, and the sequence identity (homology) of the amino acid sequence with the known cellobiohydrolase clearly showed that the AR19G-166RASFS is a novel cellobiohydrolase belonging to the GH6 family.

The AR19G-166RASFS has cellobiohydrolase activity under conditions of at least a temperature of 80° C. and a pH of 5.5. Actually, as shown in <9> of Example 1, which will be described later, the AR19G-166RASFS exhibits the cellobiohydrolase activity within a wide range of temperature from 50° C. to 95° C. The degree of cellobiohydrolase activity of the AR19G-166RASFS expressed by using *E. coli* as a host is heightened as the temperature is increased within the range of 50° C. to 95° C., and the thermostability of AR19G-166RASFS is much better than that of the AR19G-166QA and amino acid substitution variants of the AR19G-166QA.

Generally, in a protein having a certain physiological activity, deletion, substitution, or addition of at least one amino acid residue can be performed without impairing the physiological activity. In other words, in the AR19G-166RASFS, deletion, substitution, or addition of at least one amino acid residue can be performed without making the enzyme lose cellobiohydrolase activity.

That is, the super thermostable cellobiohydrolase according to the present invention is a super thermostable cellobiohydrolase having a cellobiohydrolase catalyst domain consisting any of the following (A) to (C).

(A) A polypeptide that consists of an amino acid sequence represented by SEQ ID NO:1

(B) A polypeptide that consists of an amino acid sequence formed by deletion, substitution, or addition of at least one amino acid residue in the amino acid sequence represented by SEQ ID NO:1 (here, serine in the $88^{th}$ position, phenylalanine in the $230^{th}$ position, and serine in the $414^{th}$ position in the amino acid sequence, in which the deletion, substitution, or addition of at least one amino acid residue has not yet occurred, are excluded) and has cellobiohydrolase activity under conditions of at least a temperature of 80° C. and a pH of 5.5

(C) A polypeptide that consists of an amino acid sequence (here, in the amino acid sequence, the $88^{th}$ position is serine, the $230^{th}$ position is phenylalanine, and the $414^{th}$ position is serine) having sequence identity of equal to or higher than 85% with the amino acid sequence represented by SEQ ID NO: 1 and has cellobiohydrolase activity under conditions of at least a temperature of 80° C. and a pH of 5.5

In the polypeptide (B), the number of amino acid residues in the amino acid sequence represented by SEQ ID NO:1 that undergo deletion, substitution, or addition is preferably 1 to 20, more preferably 1 to 10, and even more preferably 1 to 5.

In the polypeptide (C), the sequence identity with the amino acid sequence represented by SEQ ID NO:1 is not particularly limited as long as the sequence identity is equal to or higher than 80%. However, the sequence identity is preferably equal to or higher than 85%, more preferably equal to or higher than 90%, and even more preferably equal to or higher than 95%.

The sequence identity (homology) between amino acid sequences is obtained in the following manner. That is, in a state in which a gap is formed in positions where insertion and deletion occur, two amino acid sequences are juxtaposed with each other such that the corresponding amino acids become as identical to each other as possible; and the ratio of the identical amino acids to the total amino acid sequences excluding the gap in the obtained alignment is calculated as the sequence identity. The sequence identity between amino acid sequences can be obtained by using various homology search software known in the field of related art. In the present invention, the value of the sequence identity of the amino acid sequence is obtained by calculation based on the alignment obtained by the known homology search software BLASTP.

The polypeptides (B) and (C) may be artificially designed. Alternatively, they may be either homologues of AR19G-166 and the like or partial proteins thereof.

Each of the polypeptides (A) to (C) may be chemically synthesized based on the amino acid sequence. Alternatively, they may be produced by a protein expression system by using polynucleotides according to the present invention that will be described later. Furthermore, each of the polypeptides (B) and (C) can be artificially synthesized by using a genetic recombination technique introducing amino acid mutation, based on the polypeptide consisting of the amino acid sequence represented by SEQ ID NO:1.

The polypeptides (A) to (C) have cellobiohydrolase activity under conditions of at least a temperature of 80° C. and a pH of 5.5. The polypeptides have an extremely high degree of cellobiohydrolase activity even at a temperature of 80° C. to 100° C. Therefore, if the enzyme has any of the polypeptides (A) to (C) as a cellobiohydrolase catalyst domain, a super thermostable cellobiohydrolase can be obtained.

The super thermostable cellobiohydrolase according to the present invention has PSA as a substrate. The super thermostable cellobiohydrolase may have β glucan other than PSA as the substrate. Examples of the aforementioned other β glucans include Lichenan consisting of a β-1,3 bond and a β-1,4 bond, crystalline cellulose such as Avicel, crystalline bacteria cellulose (Bacterial microcrystalline cellulose, BMCC) and filter paper, carboxymethylcellulose (CMC), glucan consisting of a β-1,3 bond and a β-1,6 bond, glucan consisting of a β-1,3 bond, glucan consisting of a β-1,6 bond, xylan, and the like. The super thermostable cellobiohydrolase according to the present invention preferably has, as the substrate, PSA and at least one of the glucan consisting of a β-1,3 bond and a β-1,4 bond and crystalline cellulose, and more preferably has, as the substrate, PSA, glucan consisting of a β-1,3 bond and a β-1,4 bond, and crystalline cellulose.

The optimal pH of the super thermostable cellobiohydrolase according to the present invention is within a range of a pH of 5.0 to a pH of 6.5, though it varies with the reaction temperature. The super thermostable cellobiohydrolase according to the present invention preferably exhibits cellobiohydrolase activity at least within a range of a pH of 5.0 to a pH of 6.5, and more preferably exhibits cellobiohydrolase activity within a range of a pH of 4.0 to a pH of 7.0.

The super thermostable cellobiohydrolase according to the present invention may have cellulose hydrolytic activity other than the cellobiohydrolase activity. Examples of the aforementioned other cellulose hydrolytic activities include endoglucanase activity, xylanase activity, β-glucosidase activity, and the like.

The super thermostable cellobiohydrolase according to the present invention may be an enzyme including only a cellobiohydrolase catalyst domain consisting of any of the polypeptides (A) to (C), or may include other domains. Examples of other domains include domains other than a cellobiohydrolase catalyst domain that known cellobiohydrolases have. For example, the super thermostable cellobiohydrolase according to the present invention includes enzymes that are obtained by substituting the cellobiohydrolase catalyst domain of known cellobiohydrolases with the polypeptides (A) to (C).

When the super thermostable cellobiohydrolase according to the present invention includes a domain other than the cellobiohydrolase catalyst domain, it is preferable for the super thermostable cellobiohydrolase to include a cellulose-binding module. The cellulose-binding module may be positioned upstream (N terminal side) or downstream (C terminal side) of the cellobiohydrolase catalyst domain. Moreover, the cellulose-binding module and the cellobiohydrolase catalyst domain may be directly bonded to each other, or bonded to each other through a linker domain having an appropriate length. In the super thermostable cellobiohydrolase according to the present invention, the cellulose-binding module is preferably connected to the upstream or downstream of the cellobiohydrolase catalyst domain through the linker domain, and more preferably connected to the upstream of the cellobiohydrolase catalyst domain through the linker domain.

The cellulose-binding module contained in the super thermostable cellobiohydrolase according to the present invention is preferably a domain having an ability to bind to cellulose, for example, PSA or crystalline cellulose, and the amino acid sequence thereof is not particularly limited. As the cellulose-binding module, for example, cellulose-binding modules included in known proteins or domains obtained by appropriately modifying the aforementioned modules may be used. Furthermore, when the super thermostable cellobiohydrolase according to the present invention has the cellobiohydrolase catalyst domain and the cellulose-binding module, these are preferably connected to each other through a linker sequence. The amino acid sequence, the length, and the like of the linker sequence are not particularly limited. In addition, the super thermostable cellobiohydrolase according to the present invention may further have a signal peptide, which can be localized by being transferred to a specific domain in a cell, or a signal peptide, which is secreted outside a cell, on the N terminal or the C terminal. Examples of the signal peptide include an apoplastic transport signal peptide, an endoplasmic reticulum retention signal peptide, a nuclear transport signal peptide, a secretory signal peptide, and the like. Examples of the endoplasmic reticulum retention signal peptide include a signal peptide consisting of an amino acid sequence of HDEL, and the like.

Moreover, when the super thermostable cellobiohydrolase according to the present invention is produced using an expression system, in order to make it possible to simply purify the enzyme, various tags may be added to, for example, the N terminal or the C terminal. As the tags, for example, it is possible to use tags, such as a His tag, a hemagglutinin (HA) tag, a Myc tag, and a Flag tag, that are widely used for expression and purification of recombinant proteins.

[Polynucleotide Encoding Super Thermostable Cellobiohydrolase]

The polynucleotide according to the present invention encodes the super thermostable cellobiohydrolase according to the present invention. The super thermostable cellobiohydrolase can be produced by using an expression system of a host that is obtained by introducing an expression vector, into which the polynucleotide has been incorporated, into the host.

Specifically, the polynucleotide according to the present invention is a polynucleotide encoding a domain including a cellobiohydrolase catalyst domain consisting of any of the following amino acid sequences (a) to (e).

(a) A base sequence encoding a polypeptide that consists of an amino acid sequence represented by SEQ ID NO:1

(b) A base sequence encoding a polypeptide that consists of an amino acid sequence formed by deletion, substitution, or addition of at least one amino acid residue of the amino acid sequence represented by SEQ ID NO:1 (here, serine in the $88^{th}$ position, phenylalanine in the $230^{th}$ position, and serine in the $414^{th}$ position are excluded) and has cellobiohydrolase activity under conditions of at least a temperature of 80° C. and a pH of 5.5

(c) A base sequence encoding a polypeptide that consists of an amino acid sequence (herein, in the amino acid sequence, the $88^{th}$ position is serine, the $230^{th}$ position is phenylalanine, and the $414^{th}$ position is serine) having sequence identify of equal to or higher than 85% with the amino acid sequence represented by SEQ ID NO:1 and has cellobiohydrolase activity under conditions of at least a temperature of 80° C. and a pH of 5.5

(d) A base sequence encoding a polypeptide that has sequence identity of equal to or higher than 80% with an amino acid sequence represented by SEQ ID NO:2 and has cellobiohydrolase activity under conditions of at least a temperature of 80° C. and a pH of 5.5

(e) A base sequence encoding a polypeptide that is a base sequence of a polynucleotide hybridized with a polynucleotide consisting of the base sequence represented by SEQ ID NO:2 under stringent conditions and has cellobiohydrolase activity under conditions of at least a temperature of 80° C. and a pH of 5.5

In the present invention and the present specification, examples of the "stringent conditions" include the method described in Molecular Cloning-A LABORATORY MANUAL THIRD EDITION (Sambrook et al., Cold Spring Harbor Laboratory Press). For example, under the condition, in a hybridization buffer consisting of 6×SSC (composition of 20×SSC: 3 M sodium chloride, 0.3 M citric acid solution, a pH of 7.0), 5×Denhardt's solution (composition of 100× Denhardt's solution: 2% by mass of bovine serum albumin, 2% by mass of ficoll, 2% by mass of polyvinylpyrrolidone), 0.5% by mass of SDS, 0.1 mg/mL salmon sperm DNA, and 50% formamide, hybridization is performed by incubating the proteins for several hours or overnight at a temperature of 42° C. to 70° C. As a wash buffer used for washing after the incubation, a 1×SSC solution containing 0.1% by mass of SDS is preferable, and a 0.1×SSC solution containing 0.1% by mass of SDS is more preferable.

In the base sequences (a) to (e), as a degenerated codon, it is preferable to select a sequence that is highly frequently used as a codon of the host. For example, the base sequence (a) may be either the base sequence represented by SEQ ID NO:2 or a base sequence obtained by modifying the base sequence represented by SEQ ID NO:2 into the codon that is highly frequently used in the host without changing the amino acid sequence to be encoded. The modification of the codon can be performed by known genetic recombination techniques.

The polynucleotide consisting of the base sequence represented by SEQ ID NO:2 may be chemically synthesized based on base sequence information. Alternatively, the polynucleotide may be obtained by acquiring a full-length gene encoding AR19G-166 (the gene may be referred to as an "AR19G-166 gene" in some cases) or a partial domain of thereof including the cellobiohydrolase catalyst domain from nature by using a genetic recombination technique. For example, the full-length AR19G-166 gene or the partial domain thereof can be obtained in a manner in which a sample containing microorganisms is obtained from nature; and PCR is performed using a forward primer and a reverse primer designed by a common method based on the base sequence represented by SEQ ID NO:2 by using genomic DNA collected from the sample as a template. cDNA, which is synthesized by a reverse transcription reaction performed using mRNA collected from the sample as a template, may be used as a template. Furthermore, the sample, from which a nucleic acid to be a template is collected, is preferably a sample collected from an high temperature environment such as the soil of hot spring.

In the base sequence (d), the sequence identity with the base sequence represented by SEQ ID NO:2 is not particularly limited as long as it is equal to or higher than 80%. However, the sequence identity is preferably equal to or higher than 85%, more preferably equal to or higher than 90%, and even more preferably equal to or higher than 95%.

The sequence identity (homology) between base sequences is obtained in the following manner. That is, in a state in which a gap is formed in positions where insertion and deletion occur, twobase sequences are juxtaposed with each other such that the corresponding base sequences become as identical to each other as possible; and a ratio of the identical base sequences to the total base sequences excluding the gap in the obtained alignment is calculated as the sequence identity. The sequence identity between base sequences can be obtained by using various homology search software known in the field of related art. In the present invention, the value of the sequence identity of the base sequence is obtained by calculation based on the alignment obtained by the known homology search software BLASTN.

For example, each of the polynucleotides consisting of the base sequence (b) or (c) can be artificially synthesized by causing deletion, substitution, or addition of at least one base in the polynucleotide consisting of the base sequence represented by SEQ ID NO:2. Moreover, the base sequence (b) or (c) may be a full-length sequence or a partial sequence of a homologue gene of the AR19G-166 gene. The homologue gene of the AR19G-166 gene can be obtained by a genetic recombination technique used for obtaining a homologue gene of a gene of which the base sequence is already known.

The polynucleotide according to the present invention may have only the domain encoding the cellobiohydrolase catalyst domain. Alternatively, the polynucleotide may have domains encoding a cellulose-binding module, a linker sequence, various signal peptides, various tags, and the like, in addition to the aforementioned domain.

[Expression Vector]

The expression vector according to the present invention is an expression vector into which the polynucleotide according to the present invention has been incorporated and which expresses a polypeptide having cellobiohydrolase activity in a host cell under conditions of at least a temperature of 80° C. and a pH of 5.5. That is, it is an expression vector into which the polynucleotide according to the present invention has been incorporated in a state of being able to express the super thermostable cellobiohydrolase according to the present invention. Specifically, an expression cassette, which consists of DNA having a promoter sequence, the polynucleotide according to the present invention, and DNA having a terminator sequence from the upstream, needs to be incorporated into the expression vector. The polynucleotide can be incorporated into the expression vector by using known genetic recombination technique, and a commercially available expression vector preparation kit may be used.

The expression vector may be an expression vector introduced into prokaryotic cells such as E. coli or an expression vector introduced into eukaryotic cells such as yeast, filamentous fungi, insect culture cells, mammal culture cells, and plant cells. As these expression vectors, any of generally used expression vectors compatible with the host can be used.

The expression vector according to the present invention is not limited to the polynucleotide according to the present invention, and is preferably an expression vector into which a drug-resistant gene or the like has been incorporated. This is because such an expression vector makes it easy to select a host having undergone transformation and a host having not undergone transformation.

Examples of the drug-resistant gene include a kanamycin-resistant gene, a hygromycin-resistant gene, a bialaphos-resistant gene, and the like.

[Transformant]

The transformant according to the present invention contains the expression vector according to the present invention introduced thereinto. In the transformant, the super thermostable cellobiohydrolase according to the present invention can be expressed. The cellobiohydrolases known in the related art are expressed only in a narrow range of expression hosts. That is, many of the cellobiohydrolases are not easily expressed in different types of host cells. In contrast, the super thermostable cellobiohydrolase according to the present invention can be expressed in a wide range of expression cells such as *E. coli*, yeast, filamentous fungi, and the chloroplast of higher plants. That is, the transformant according to the present invention includes *E. coli*, yeast, filamentous fungi, the chloroplast of higher plants, and the like into which the expression vector of the present invention has been introduced.

The method for preparing the transformant by using the expression vector is not particularly limited, and can be performed by methods generally used fir preparing transformants. Examples of the methods include an agrobacterium method, a particle gun method, an electroporation method, a polyethylene glycol (PEG) method, and the like. When the host is a plant cell, it is preferable to use a particle gun method or an agrobactrium method among the above methods.

In another aspect, the host into which the expression vector is introduced may be prokaryotic cells such as *E. coli* or eukaryotic cells such as yeast, filamentous fungi, insect culture cells, mammal culture cells, and plant cells. By culturing transformants of *E. coli*, the super thermostable cellobiohydrolase according to the present invention can be mass-produced more simply. Meanwhile, in eukaryotic cells, the protein undergoes glycosylation. Therefore, if transformants of the eukaryotic cells are used, a super thermostable cellobiohydrolase superior in thermostability is obtained, compared to a case of using the transformants of the prokaryotic cells. Particularly, when the transformants are eukaryotic microorganisms such as a filamentous fungus like *Aspergillus* or yeast, a super thermostable cellobiohydrolase superior in thermostability can be mass-produced in a relatively simple manner.

When prokaryotic cells, yeast, filamentous fungi, insect culture cells, mammal culture cells, and the like are used as host, generally the obtained transformants can be cultured by a common method in the same manner as used for the host having not undergone transformation.

When the transformant according to the present invention is a plant, as the host, plant culture cell, plant organs, or plant tissues may be used. By using known plant tissue culture methods and the like, transformed plants can be obtained from transformed plant cells, callus, and the like. For example, if transformed plant cells are cultured by using a hormone-free redifferentiation medium, and the obtained young plant, which has taken root, is transplanted into soil or the like and cultivated, a transformed plant can be obtained.

[Method for Manufacturing Super Thermostable Cellobiohydrolase]

The method for manufacturing a super thermostable cellobiohydrolase according to the present invention is a method for producing a super thermostable cellobiohydrolase in the transformant according to the present invention. In the transformant manufactured by using the expression vector, into which the polynucleotide according to the present invention has been incorporated into the downstream of a promoter that is not able to control the time of expression or the like, the super thermostable cellobiohydrolase according to the present invention is expressed constantly. In contrast, a transformant manufactured using a so-called expression induction-type promoter, which induces expression depending on a specific compound, temperature conditions, and the like, is subjected to induction treatment appropriate for the respective expression conditions, and in this way, the super thermostable cellobiohydrolase is expressed in the transformant.

The super thermostable cellobiohydrolase produced by the transformant may be used in a state of being held in the transformant or may be extracted or purified from the transformant.

The method for extracting and purifying the super thermostable cellobiohydrolase from the transformant is not particularly limited as long as it is a method that does not impair the activity of the super thermostable cellobiohydrolase. The super thermostable cellobiohydrolase can be extracted by a method that is generally used for extracting polypeptides from cells or biological tissues. Examples of the method include a method of dipping the transformant in an appropriate extraction buffer, extracting the super thermostable cellobiohydrolase, and then separating the enzyme into an extract and a solid residue. The extraction buffer preferably contains a solubilizing agent such as a surfactant. When the transformant is a plant, the transformant may be shred or fragmented before being dipped in the extraction buffer. Furthermore, as the method for separating the enzyme into an extract and a solid residue, for example, it is possible to use known solid-liquid separation treatment such as a filtration method, a compression filtration method, and a centrifugation method. Moreover, the transformant in a state of being dipped in the extraction buffer may be squeezed. The super thermostable cellobiohydrolase in the extract can be purified using a known purification method such as a salting-out method, an ultrafiltration method, and a chromatography method.

When the super thermostable cellobiohydrolase according to the present invention is expressed in a state of having a secretory signal peptide in the transformant, by culturing the transformant and then collecting culture supernatant excluding the transformant from the obtained culture, a solution containing the super thermostable cellobiohydrolase can be simply obtained. Moreover, when the super thermostable cellobiohydrolase according to the present invention has a tag such as a His tag, the super thermostable cellobiohydrolase in the extract or the supernatant can be simply purified by an affinity chromatography method using the tag.

[Cellulase Mixture]

The super thermostable cellobiohydrolase according to the present invention or the super thermostable cellobiohydrolase manufactured by the method for manufacturing a super thermostable cellobiohydrolase according to the present invention can also be used as a cellulase mixture containing at least one other kind of cellulase. The super thermostable cellobiohydrolase manufactured by the method for manufacturing a super thermostable cellobiohydrolase according to the present invention may be used in a state of being contained in the transformant or may be extracted or purified from the transformant. If the super thermostable cellobiohydrolase according to the present invention is used as a mixture, which contains another cellulase, for a cellulose degradation reaction, recalcitrant lignocellulose can be more efficiently degraded.

The aforementioned another cellulase other than the super thermostable cellobiohydrolase that is contained in the cellulase mixture is not particularly limited as long as the cellulase exhibits hydrolytic activity with respect to cellulose. Examples thereof include a hemicellulase such as xylanase or β-xylosidase, β-glucosidase, endoglucanase, and the like. The cellulase mixture according to the present invention preferably contains at least one of the hemicellulase and endoglucanase and more preferably contains both the hemicellulase and endoglucanase. Particularly, the cellulase mixture preferably contains at least one kind selected from the group consisting of xylanase. β-xylosidase, β-glucosidase, and endoglucanase, and more preferably contains all of the xylanase, β-xylosidase, β-glucosidase, and endoglucanase.

The aforementioned another cellulase contained in the cellulase mixture is preferably a thermostable cellulase having cellulase activity at a temperature of at least 70° C., and more preferably a thermostable cellulase having cellulase activity at a temperature of at least 70° C. to 90° C. If all of the enzymes contained in the cellulase mixture are resistant to heat, the degradation reaction of cellulose performed using the cellulase mixture can be efficiently performed under altithermal conditions. That is, when the cellulase mixture contains only thermostable cellulases, if the cellulase mixture is used for hydrolysis of lignocellulose, a hydrolysis reaction of lignocelluloses can be performed under an altithermal condition at a hydrolysis temperature of 70° C. to 90° C. By the hydrolysis performed under the high temperature condition, the amount of enzyme and the time taken for hydrolysis can be markedly decreased, and the hydrolysis cost can be greatly reduced.

[Method for Manufacturing Cellulose Degradation Product]

The method for manufacturing a cellulose degradation product according to the present invention is a method for obtaining a degradation product by degrading cellulose by using the super thermostable cellobiohydrolase according to the present invention. Specifically, by bringing a cellulose-containing material into contact with the super thermostable cellobiohydrolase according to the present invention, the transformant according to the present invention, or the super thermostable cellobiohydrolase manufactured by the method for manufacturing a super thermostable cellobiohydrolase according to the present invention, a cellulose degradation product is produced.

Herein, the term "cellulose degradation product" means a cello-oligosaccharide containing mainly cellobiose, cellotriose and the like.

The cellulose-containing material is not particularly limited as long as it contains cellulose. Examples of the material include cellulose-based biomass such as weeds and agricultural waste, waste paper, and the like. Before being brought into contact with the super thermostable cellobiohydrolase according to the present invention, the cellulose-containing material is preferably subjected to physical treatment such as fragmentation or shredding and chemical treatment using an acid, an alkali, and the like, dipped in an appropriate buffer, or subjected to a dissolution treatment.

The reaction condition of the hydrolysis reaction of the cellulose performed by the super thermostable cellobiohydrolase according to the present invention is preferably a condition under which the super thermostable cellobiohydrolase exhibits cellobiohydrolase activity. For example, the reaction is preferably performed under conditions of a temperature of 55° C. to 100° C. and a pH of 3.5 to 7.0, and more preferably performed under conditions of a temperature of 70° C. to 100° C. and a pH of 4.0 to 6.0. The reaction time is appropriately adjusted in consideration of the type of the cellulose-containing material used for the hydrolysis reaction, the pretreatment method of the material, the amount of the material, and the like. For example, the reaction may be performed for 10 minutes to 100 hours. In the case of degrading cellulose-based biomass, the reaction can be performed for 1 hour to 100 hours.

For the hydrolysis reaction of cellulose, in addition to the super thermostable cellobiohydrolase according to the present invention, at least one other kind of cellulase is preferably used. As the aforementioned another cellulase, the same cellulase as the cellulase contained in the cellulase mixture can be used, and the cellulase is preferably thermostable cellulase which has cellulase activity at a temperature of at least 70° C. and more preferably at a temperature of at least 70° C. to 100° C. Furthermore, in the method for manufacturing the cellulose degradation product, instead of the super thermostable cellobiohydrolase according to the present invention, the transformant according to the present invention, or the super thermostable cellobiohydrolase manufactured by the method for manufacturing a super thermostable cellobiohydrolase according to the present invention, the aforementioned cellulase mixture may be used.

EXAMPLES

Next, the present invention will be more specifically described based on examples, but the present invention is not limited to the following examples.

Example 1

Cloning of Novel Super Thermostable Cellobiohydrolase from Soil of Hot Spring

<1> Preparation of Metagenomic DNA of High Temperature Soil

From an area in Japan from which high temperature hot spring gushes out, hot spring water containing soil, mud, and biomass was collected. The temperature and pH of the just collected samples were in a range of 33° C. to 78° C. and 7.2 to 8 respectively. Among the samples of soil of hot spring, five samples named AR19, OJS2, OJS4, OJS7, and OJS9 respectively as metagenomic DNA samples were subjected to DNA extraction. From 10 g of each of the collected samples of soil of hot spring, DNA was extracted by using a DNA extraction kit (ISOIL Large for Beads ver. 2, NIPPON GENE CO., LTD.). From AR19, DNA was obtained in an amount of equal to or greater than 10 μg, and metagenomic sequencing was performed on 5 μg of the DNA by using GS FLX Titanium 454 manufactured by Roche Diagnostics. The remaining DNA was used for PCR cloning of cellulase genes. Meanwhile, the samples, from which a small amount (equal to or less than 10 μg) DNA was obtained, were subjected to genome amplification by using a genomic DNA amplification kit (GenomiPhi V2 DNA Amplification Kit, manufactured by GE Healthcare).

<2> Assembly and Statistic of Metagenomic Data of Soil of Hot Spring

By using AR19 as one of the genomic DNA samples extracted from the metagenomes of soil of hot spring, shotgun sequencing was performed three times according to the standard protocol of shotgun sequencing of 454 GS FLX Titanium technology manufactured by Roche. The output (sff file) of the Roche 454 was subjected to re-base calling by PyroBayes (Quinlan et al., Nature Methods, 2008, vol. 5, p. 179-81.), and as a result, FASTA format sequence files and Quality-value files were obtained. The ends of the obtained sequence reads were cut off so as to improve the quality thereof, and the sequence reads were assembled by using assembly software Newbler version 2.3 of 454 Life Science. The assembly was performed under conditions set to be "minimum acceptable overlap match (mi)=0.9", "option:— large (for large or complex genomes, speeds up assembly, but reduces accuracy.)".

The reads having undergone Quality filtering processing and assembled contigs having a length of equal to or greater than 100 bp had a length of 330 Mbp in total, and the data set was used for cellulase enzyme gene analysis. Among a total of 2,766,332 reads, 2,040,651 reads were assembled into contigs (101,372 contigs in total) having a length of equal to or greater than 1,027 bp on average, and among these, the longest contig had a length of 187,970 bp.

For the assembled sequences, all of the contigs and singletons were phylogenetically classified into five categories including bacteria, archea (archacbacteria), prokaryote, virus, and a group belonging to none of these, with reference to KEGG database (Kanehisa, M. Science & Technology Japan, 1996, No. 59, p. 34-38, http://www.genome.jp/kegg/, 2011/5/11 (searched)). In the length of 330 Mbp (=total contig length+total singleton length) of the assembled sequence, the length of the sequence hit into bacteria was 59.9 Mbp, the length of the sequence hit into archea was 3.1 Mbp, the length of the sequence hit into prokaryote was 25,499 bp, and the length of the sequence hit into virus was 384,255 bp. These results evidently showed that the metagenomic database included only 19.2% of the known DNA sequence. The length of the sequence belonging to none of the above categories was 266.7 Mbp and accounted for 80.8% of the entire assembled sequence. These are novel sequences derived from any of bacteria, archea, and prokaryote.

<3> Open Reading Frame (ORF) Prediction of Cellobiohydrolase

From UniProt database (http://www.uniprot.org/), sequences of EC Nos. 3.2.1.4 (cellulase), 3.2.1.37 (β-xylosidase), 3.2.1.91 (cellulose 1.4-β-cellobiosidase), and 3.2.1.8 (endo 1,4-β-xylanase) were downloaded (access number: 2009/4/13), and a proteomic local database of these glycoside hydrolase genes was constructed. By using annotation software Orphelia (Hoff et al., Nucleic Acids Research, 2009, 37 (Web Server issue: W101-W105)), a gene domain (=open reading frame) was estimated from the contig sequences obtained in the section <2> (Orphelia option: default (model=Net 700, maxoverlap=60)). In order to extract glycoside hydrolase genes from the estimated ORF, BLASTP (blastall ver. 2.2.18) was used, and the local database was referred to. The option conditions of BLASTP were set to be "Filter query sequence=false", "Expectation value (E)<$1e^{-20}$", "default values: Cost to open a gap=−1, Cost to extended gap=−1, X dropoff value for gapped alignment=0, Threshold for extending hits=0, Word size=default", and the hit sequences were collected as glycoside hydrolase genes.

The glycoside hydrolases, such as cellulase, endohemicellulase, and debranching enzymes, obtained in the aforementioned manner were subjected to functional classification based on pfam HMMs (Pfam version 23.0 and HMMER v 2.3 Finn et al., Nucleic Acids Research Database, 2010, Issue 38, p. D211-222) as functional domain sequence database of proteins. Specifically, by using a sequence homology search algorithm HMMER (Durbin et al., 'The theory behind profile HMMs. Biological sequence analysis: probabilistic models of proteins and nucleic acids', 1998, Cambridge University Press.; hmmpfam (Ver. 2.3.2), E-value cutoff <$1e^{-5}$; Database=Pfam_fs (models that can be used to find fragments of the represented domains in a sequence)) using a hidden Markov model, the sequences were classified into a glycoside hydrolase (GH) family based on the homology thereof with the Pfam domain database.

<4> Cloning of AR19G-166RA and AR19G-166QV

From the metagenome AR19 of the soil of hot spring, thirteen ORFs including cellobiohydrolase catalyst domain sequence belonging to GH6. GH9, GH48, and other GH families were obtained. For these ORFs, primers were designed, and the genes were cloned from the metagenome AR19 of the soil of hot spring by means of PCR. From the open reading frame AR19G-166, cellobiohydrolase genes (AR19G-166RA and AR19G-166QV) belonging to the GH6 family were cloned.

<5> Open Reading Frame AR19G-166

The open reading frame AR19G-166 encoded a polypeptide (SEQ ID NO:5) consisting of 474 amino acid residues. However, AR19G-166 consisted of an incomplete sequence in which the start codon was lost, and was constituted only with the partial sequence of a linker and the GH6 catalyst domain. The GH6 catalyst domain of AR19G-166 was cloned into the genes AR19G-166RA and AR19G-166QV by PCR cloning, and exhibited 66% of amino acid sequence identity with respect to a GH6 glycoside hydrolase (Genbank: ABX 04776.1) of *Herpetosiphon aurantiacus* DSM 785 as a mesophilic thermophilic bacterium in the phylum Chlroflexi. By PCR cloning using a forward primer consisting of a base sequence represented by SEQ ID NO:7 (5'-CACCATGTTGGACAATCCATTCATCGGAG-3': obtained by adding seven bases (CACCATG) to the 5'-terminal side of a base sequence represented by SEQ ID NO:6; in the added sequence, ATG at the 3' side is a start codon, and CACC at the 5' side is a sequence for being inserted into a vector) and a reverse primer consisting of a base sequence represented by SEQ ID NO:8 (5'-TAGGGTTGGATCG-GCGGATAG-3'), two gene clones (AR19G-166RA and AR19G-166QV) were obtained from AR19G-166. The amino acid sequences encoded by AR19G-166RA and AR19G-166QV were different from each other only in terms of two amino acid residues in the $299^{th}$ position and the $351^{st}$ position. In AR19G-166RA, the amino acid residue in the $299^{th}$ position was arginine, and the amino acid residue in the $351^{st}$ position was alanine. In AR19G-166QV, the amino acid residue in the $299^{th}$ position was glutamine, and the amino acid residue in the $351^{st}$ position was valine.

<6> PCR Cloning of Natural Variant

The aforementioned five metagenomic DNA (AR19, OJS2, OJS4, OJS7, and OJS9) were subjected to PCR cloning of cellobiohydrolase genes by using a forward primer consisting of the base sequence represented by SEQ ID NO:7 and a reverse primer consisting of the base sequence represented by SEQ ID NO:8. The sequence of the hit clones was decoded by a Sanger sequencer. The genotype and amino acid mutation of each of the clones are shown in Tables 1 and 2. By performing PCR cloning on a plurality of metagenomic DNA samples, a total of forty-six clones of natural variants having a large number of SNPs were obtained. These variants showed SNPs in a total of twenty-seven sites including c6t, g51a, a69g, a201g, c259t, c433t, c450t, g456c, c531t, a627g, a896g, c1116t, c98t (A33V), t251c (184T), c262t (P88S), g497a (R166H), c683t (T228I), c688t (L230F), a762t (E254D), a761g (E254G), c805t (R269C), a896g (R299Q), a916g (S306G), c1052t (A351V), a1078g (E360K), g1216a (A406T), and t1241c (F414S) (SNP is represented by in small letters, and the letters in the parenthesis represent amino acid substitution caused by SNP). The SNP caused amino acid substitution in fourteen sites among the twenty-seven sites (Tables 1 and 2). In all of the clones showing the SNP, IN/DEL mutation (insertion and deletion of a DNA base sequence) was not observed.

TABLE 1

|  | Metagenome DNA samples | | | | | |
|---|---|---|---|---|---|---|
|  | AR19 | OJS2 | OJS4 | OJS5 | OJS9 | Total |
| No. of clones amplified by colony PCR | 240 | 48 | 48 | 48 | 48 | 432 |
| No. of clones hit | | | | | | |
| QA (Q299/A351) | 18 | 3 | 4 | 3 | 1 | 29 |
| QV (Q299/V351) | 1 | 0 | 0 | 0 | 0 | 1 |
| RA (R299/A351) | 4 | 0 | 0 | 0 | 0 | 4 |
| QA/A33V | 2 | 0 | 0 | 0 | 0 | 2 |
| QA/T228I | 0 | 0 | 1 | 0 | 0 | 1 |
| QA/R269C | 1 | 0 | 0 | 0 | 0 | 1 |
| QA/E254G | 0 | 0 | 0 | 1 | 0 | 1 |
| QA/S306G | 2 | 0 | 0 | 0 | 0 | 2 |
| QA/R166H/B360K | 0 | 0 | 1 | 0 | 0 | 1 |
| QA/I84T/A406T | 0 | 0 | 0 | 1 | 0 | 1 |
| RA/E254D | 1 | 0 | 0 | 0 | 0 | 1 |
| RA/P88S/L230F/F414S | 0 | 2 | 0 | 0 | 0 | 2 |
| Total No. of clones hit | 29 | 5 | 6 | 5 | 1 | 46 |

TABLE 2

| Clone variants | SNPs and amino acid substitutions |
|---|---|
| Among QA lones | c6t, a201g, c259t, c450t, g456c, c531t, a627g |
| QV | c1052t (A351V) |
| RA | a51g, a201g, a896g (Q299R) |
| QA/A33V | c98t (A33V) |
| QA/T228I | a201g, c433t, c683t(T228I), c1116t |
| QA/R269C | c805t (R269C) |
| QA/E254G | a201g, a761g (E254G) |
| OA/S306G | a69g, a916g (S306G) |
| QA/R166H/E360K | a201g, g497a (R166H), a1078a (E360K) |
| QA/I84T/A406T | a201g, 251c (I84Tt), g1216a (A406T) |
| RA/E254D | a51g, a201g, a762t (E254D), a896g (Q299R) |
| RA/P88S/L230F/F414S | a201g, c262t (P88S), c688t (L230F), a896g (Q299R), t1241c (F414S) |

Among the forty-six clones obtained as above, twenty-nine clones, which were more than half of the clones, were variants AR19G-166QA (hereinafter, abbreviated to "QA", SEQ ID NO:3) encoding an amino acid sequence in which the amino acid residue in the $299^{th}$ position was glutamine and the amino acid residue in the $351^{st}$ position was alanine; one clone was a variant AR19G-166QV (hereinafter, abbreviated to "QV", SEQ ID NO:9) encoding an amino acid sequence in which the amino acid residue in the $299^{th}$ position was glutamine and the amino acid residue in the $351^{st}$ position was valine; and four clones were variants AR19G-166RA (hereinafter, abbreviated to "RA", SEQ ID NO:10) encoding an amino acid sequence in which the amino acid residue in the $299^{th}$ position was arginine and the amino acid residue in the $351^{st}$ position was alanine (Table 1).

Twelve other clones were variants formed by mutation of one to three amino acid residues in QA, RA, or OV. Among the twelve clones, nine clones were variants formed by substitution of one to two amino acid residues in the amino acid sequence encoded by AR19G-166QA (Table 1). The nine clones included two QA/A33V clones in which alanine in the $33^{rd}$ position was substituted with valine; one QA/T228I clone in which threonine in the $228^{st}$ position was substituted with isoleucine; one QA/R269C clone in which arginine in the $269^{th}$ position was substituted with cysteine; one QA/E254G clone in which glutamic acid in the $254^{th}$ position was substituted with glycine; two QA/S306G clones in which serine in the $306^{th}$ position was substituted with glycine; one QA/R166H/E360K clone in which arginine in the $166^{th}$ position and glutamic acid in the $360^{th}$ position were substituted with histidine and glycine respectively; and one QA/I84T/A406T clone in which isoleucine in the $84^{th}$ position and alanine in the $406^{th}$ position were substituted with threonine.

Three other clones were variants formed by substitution of one or three amino acid residues in the amino acid sequence encoded by AR19G-166RA. These clones included one RA/E254D clone in which glutamic acid in the $254^{th}$ position was substituted with aspartic acid; and two RA/P88S/L230F/F414S clones (also referred to as "AR19G-166RASFS", SEQ ID NO:1) in which proline in the $88^{th}$ position, leucine in the $230^{th}$ position, and phenylalanine in the $414^{th}$ position were substituted with serine, phenylalanine, and serine respectively.

FIG. 1 shows the sequence alignment of amino acid residues encoded by AR19G-166RA, AR19G-166QV, AR19G-166QA, and AR19G-166RASFS. These four kinds of genes were genes cloned from five metagenomic samples of high temperature soil by PCR cloning by using the same primer set. In the drawing, "•" represents the same amino acid residue, and the substituted amino acid residues are represented by white letters.

AR19G-166QA was the clone that most frequently appeared, and a total of twenty-nine clones of AR19G-166QA were obtained from the five kinds of metagenomic DNA (Table 2). The twenty-nine AR19G-166QA clones included SNPs at seven sites (c6t, a201g, c259t, c450t, g456t, c531 t, and a627g) in the base sequence.

Unlike the AR19G-166QA genes, the base sequence of AR19G-166RA genes included SNPs at three sites (a51g, a201g, and a896g) (Table 2). Among these, two sites were silent mutation, and guanine at both the $51^{st}$ position and the $201^{st}$ position of the base sequence were substituted with adenine. The remaining one site was SNP involved in amino acid substitution, and adenine in the $896^{th}$ position was mutated into guanine. Due to the SNP, in AR19G-166RA, the amino acid residue in the $299^{th}$ position in the amino acid sequence was substituted with arginine.

The base sequence of the AR19G-166QV genes included SNP at one site (Table 2). In the base sequence, cytosine in the $1,052^{nd}$ position was mutated into thymine. Consequentially, in AR19G-166QV, the amino acid residue in the $351^{st}$ position of the amino acid sequence encoded by AR19G-166QA was substituted with valine.

Among the twelve kinds of AR19G-166SNP variants, AR19G-166RASFS exhibiting strongest thermostability included SNPs at five sites (a201 g, c262t (P88S), c688t (L230F), a896g (Q299R), and t1241c (F414S)) unlike AR19G-166QA (Table 2). Among these, four sites were involved in amino acid substitution. At one site among the four sites, adenine in the $896^{th}$ position was mutated into guanine similarly to AR19G-166RA, and the amino acid residue in the $299^{th}$ position in the amino acid sequence encoded by AR19G-166RASFS was substituted with arginine. At three other sites, cytosine in the $262^{nd}$ position was mutated into thymine, cytosine in the $688^{th}$ position was mutated into thymine, and thymine in the $1241^{st}$ position was mutated into cytosine. Due to the SNPs, in the amino acid sequence encoded by AR19G-166RASFS, proline in the $88^{th}$ position was substituted with serine, leucine in the $230^{th}$ position was substituted with phenylalanine, and phenylalanine in the $414^{th}$ position was substituted with serine.

<7> Expression and Purification of Amino Acid Substitution Natural Variant

Plasmids obtained by PCR cloning were introduced into a Rosetta-gamiB (DE3) pLysS strain (manufactured by Merck & Co., Inc) of *E. coli* for protein expression by a heat shock method. *E. coli* having target genes was inoculated into an LB medium containing ampicillin at 100 mg/L and cultured until $OD_{600}$ became about 0.2 to 0.8. Thereafter, IPTG (Isopropyl-β-D(−)-thiogalactopyrandoside) was added thereto, and the bacterium was cultured for 20 hours to induce expression of target proteins. After culturing, *E. coli* was collected by performing centrifugation, and 200 mM acetate buffer (a pH of 5.5) having a volume of 1/20 of the volume of the culture fluid was added thereto so as to suspend the bacterium. Subsequently, by using an ultrasonic fragmentation device BioRuptor UCD-200T (manufactured by COSMO BIO CO., LTD.), the resultant was subjected to fragmentation for 30 seconds, and then the fragmentation was stopped for 30 seconds. The treatment process was repeated 10 times, and as a result, supernatant containing the target proteins having undergone amino acid substitution was obtained. The supernatant was taken as a crude enzyme sample liquid.

The target proteins in the crude enzyme sample liquid were confirmed by SDS-PAGE analysis. FIG. 2 shows the results of the SDS-PAGE analysis (CBB staining) of cellobiohydrolase enzyme proteins encoded by natural variants of the AR19G-166 genes.

An ion exchange column HiTrap Q HP (manufactured by GE Healthcare) equilibrated using 50 mM Tris-HCl buffer (a pH of 8.0) was filled with the crude enzyme sample liquid. Thereafter, by using a medium/high-pressure liquid chromatography system AKTA design (manufactured by GE Healthcare) and 50 mM Tris-HCl buffer (a pH of 8.0) containing 1 M NaCl, proteins were fractionated at a concentration gradient of 0% to 50%. The fractions having cellobiohydrolase activity were mixed together, and then the solution thereof was exchanged with 50 mM Tris-HCl buffer (a pH of 8.0) containing 750 mM ammonium sulfate by using a centrifugal ultrafiltration membrane VIVASPIN 20 (manufactured by Sartorius Stedim Biotech). Then a hydrophobic interaction separation column HiTrap Phnenyl HP (manufactured by GE Healthcare) equilibrated using the same butter was filled with the fraction having cellobiohydrolase activity having undergone the solution exchange, and proteins were extracted at a concentration gradient of 100% to 0% by using 50 mM Tris-HCl buffer (a pH of 8.0). The fractions having cellobiohydrolase activity were mixed together and then concentrated using VIVASPIN 20 until the liquid amount thereof became about 8 mL. The concentrated sample was added to a gel filtration column Hiload 26/60 superdex 200 pg (manufactured by GE Healthcare) equilibrated using 50 mM Tris-HCl buffer (a pH of 8.0) containing 150 mM NaCl, and fractionation was performed by causing the same buffer having volume 1 to 1.5 times greater than that of the column to flow at a rate of 2 mL/min to 3 mL/min. After the fractions having cellobiohydrolase activity were mixed together, the solution thereof was exchanged with 50 mM Tris-HCl buffer (a pH of 8.0), followed by concentration, thereby obtaining a purified enzyme sample liquid having final concentration of about 1 mg/mL.

<8> Measurement of Cellobiohydrolase Activity having PSA as Substrate (PSA Hydrolytic Activity)

For measuring the cellobiohydrolase activity, phosphoric acid-swollen Avicel (PSA) was used as a substrate. PSA was prepared in a manner in which Avicel powder (fine crystalline cellulose powder, manufactured by Merck & Co., Inc) was dissolved in a phosphoric acid solution; sterilized distilled water was then added thereto to precipitate the crystals, and the crystals were washed until the pH thereof became equal to or greater than 5.0. All of the PSA used in the following experiment was prepared in this manner.

A reaction solution for measuring the PSA activity was composed of a PSA solution having final concentration of 0.5%, 50 mM acetate buffer (a pH of 5.5), and the crude enzyme sample liquid (prepared in the section <7>) diluted appropriately. The reaction solution was reacted for 20 minutes at a temperature of 50° C. to 90° C. After the reaction ended, the amount of the reducing end hydrolyzed using 3,5-dinitrosalicyclic acid reagent (DNSA) was measured by a spectrophotometer (540 nm), and by using a calibration curve created using glucose, the amount of reduced sugar was calculated. Thereafter, from the difference in the amount between a control section and an experimental section, the amount of reduced sugar generated by hydrolysis of the enzyme was calculated. The maximum amount of the reduced sugar was regarded as being 100, and the amount of the reduced sugar at each temperature was plotted as a relative value.

Figure 3:
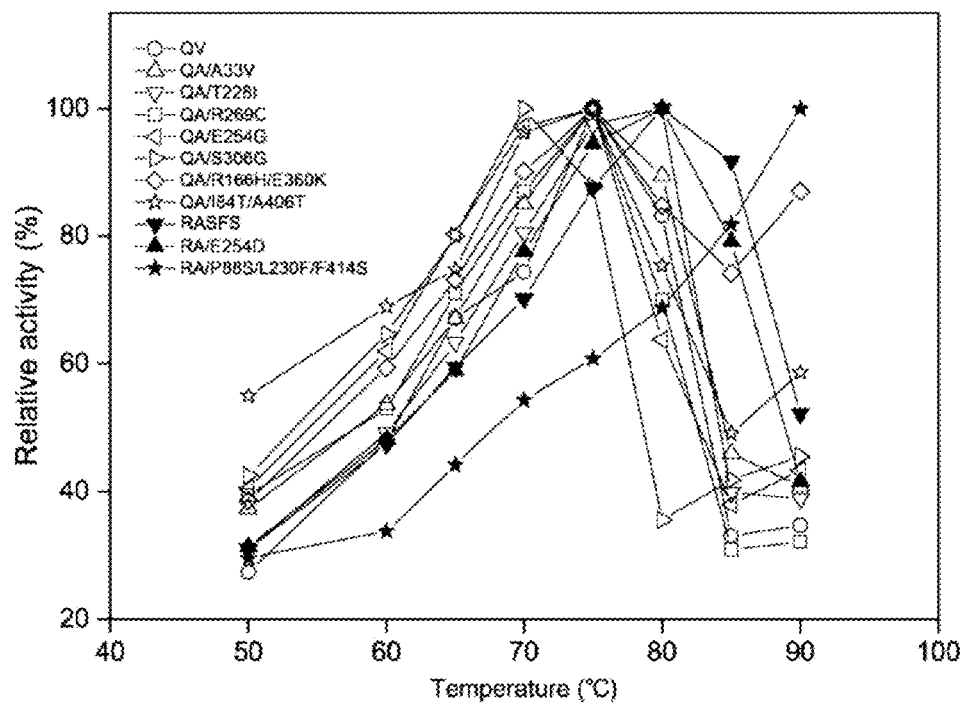
FIG. 3 is a view showing results obtained by measuring PSA hydrolytic activity of cellobiohydrolase enzyme proteins encoded by the natural variants of the AR19G-166 gene in Example 1.

FIG. 3 shows the results obtained by measuring PSA activity. All of the amino acid substitution variants of the cellobiohydrolase enzyme gene AR19G-166 cloned from the metagenomic DNA of high temperature soil exhibited PSA hydrolytic activity. The optimal temperature of the amino acid substitution variants of AR19G-166QV and AR19G-166QA was lower than that of AR19G-166RA and the amino acid substitution variants of AR19G-166RA. In QA/T228I, $T_{opt}$=80° C.; in QA/S306G, $T_{opt}$=70° C.; and in other amino acid substitution variants of AR19G-166QA, $T_{opt}$=75° C. In contrast, in AR19G-166RA and RA/E254D as an amino acid substitution variant thereof, $T_{opt}$=80° C.; and in AR19G-166RASFS as an amino acid substitution variant of AR19G-166RA, $T_{opt}$>90° C.

In the DE method that artificially causes mutation, a large number of loss-of-function variants are generated, hence functional assay becomes useless in many cases. However, all of the large number of variants cloned by the natural variant obtaining method according to the present invention had enzyme activity, and the cellobiohydrolase AR19G-166RASFS exhibiting heat stability of equal to or higher than 15° C. was obtained from the variant library constituted with a relatively small number of clones.

<9> Examination on Enzyme Characteristics

The enzyme proteins of the variant AR19G-166RASFS, which was confirmed to have the highest optimal temperature $T_{opt}$ in the PSA hydrolytic activity assay and formed by substitution of three amino acids (P88S/L230F/F414S) of AR19G-166RA, were purified, and regarding the substrate specificity, pH characteristics, temperature characteristics (optimal temperature and heat stability), the enzyme characteristics were specifically measured.

(Substrate Specificity)

The substrate specificity was measured by using Avicel powder, carboxymethyl cellulose (CMC, manufactured by Sigma-Aldrich Co, LLC.), xylan (from Beechwood, manufactured by Sigma-Aldrich Co, LLC.), Lichenan (manufactured by MP Biomedicals LLC.), and Laminarin (from *Laminaria digitata*, manufactured by Sigma-Aldrich Co. LLC.). The reaction solution was composed of 100 μL of a 1% aqueous solution of each substrate, 50 μL of 200 mM acetate buffer (a pH of 5.5), 40 μL of purified water, and 10 μL of the purified enzyme sample liquid. The reaction solution was reacted for 20 minutes at 70° C. In the same manner as in the section <8>, the amount of reduced sugar generated by the hydrolysis of the enzyme was calculated, and specific activity (U/mg) was calculated. Each measurement was performed three times independently, and the average and standard error were calculated.

Figure 4:
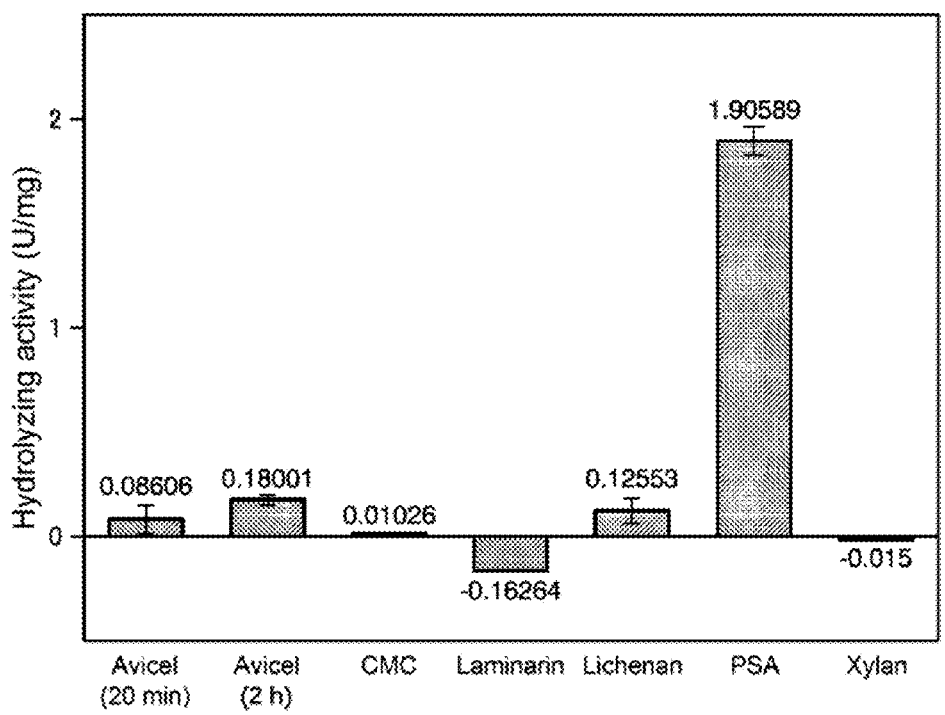
FIG. 4 is a view showing results obtained by measuring cellobiohydrolase activity of AR19G-166RASFS with respect to the respective substrates in Example 1.

FIG. 4 shows the measurement results. AR19G-166RASFS exhibited a high degree of hydrolytic activity with respect to the water-soluble phosphoric acid-swollen Avicel PSA (1.90589 U/mg), and exhibited degradation activity with respect to Lichenan consisting of glucan having a β-1,3 bond and a β-1,4 bond (0.12553 U/mg). In contrast, AR19G-166RASFS practically did not exhibit degradation activity with respect to CMC (0.01026 U/mg) or Laminarin consisting of glucan having a β-1,3 bond and a β-1,6 bond (−0.16264 U/mg). Although AR19G-166RASFS exhibited extremely weak hydrolytic activity with respect to the crystalline cellulose Avicel (0.08606 U/mg), it exhibited marked hydrolytic activity in the assay in which the reaction was performed for 2 hours (0.18001 U/mg). AR19G-166RASFS did not exhibit hydrolytic activity with respect to xylan (−0.015 U/mg).

(Temperature Dependency)

The temperature dependency of PSA hydrolytic activity of AR19G-166RASFS was investigated. For measuring the PSA hydrolytic activity, a reaction solution composed of 100 μL of a 1% PSA solution, 50 μL of an acetate buffer (a pH of 5.5), 40 μL of purified water, and 10 μL of the purified enzyme sample liquid was used, and the reaction solution was reacted for 20 minutes at a temperature of 50° C. 60° C., 65° C., 70° C., 75° C., 80° C., 85° C., 90° C., 95° C., or 99° C. The amount of reduced sugar generated by the hydrolysis reaction of the enzyme was calculated. Moreover, the enzyme activity by which 1 μmol of reduced sugar is generated for 1 minute was regarded as being 1 U, and the value obtained be dividing the enzyme activity by the protein amount was taken as specific activity (U/mg). Furthermore, 0.5 mM calcium ions or 0.5 mM manganese ions were added to the reaction solution, and the PSA hydrolytic activity was measured in the same manner as described above.

Figure 5:
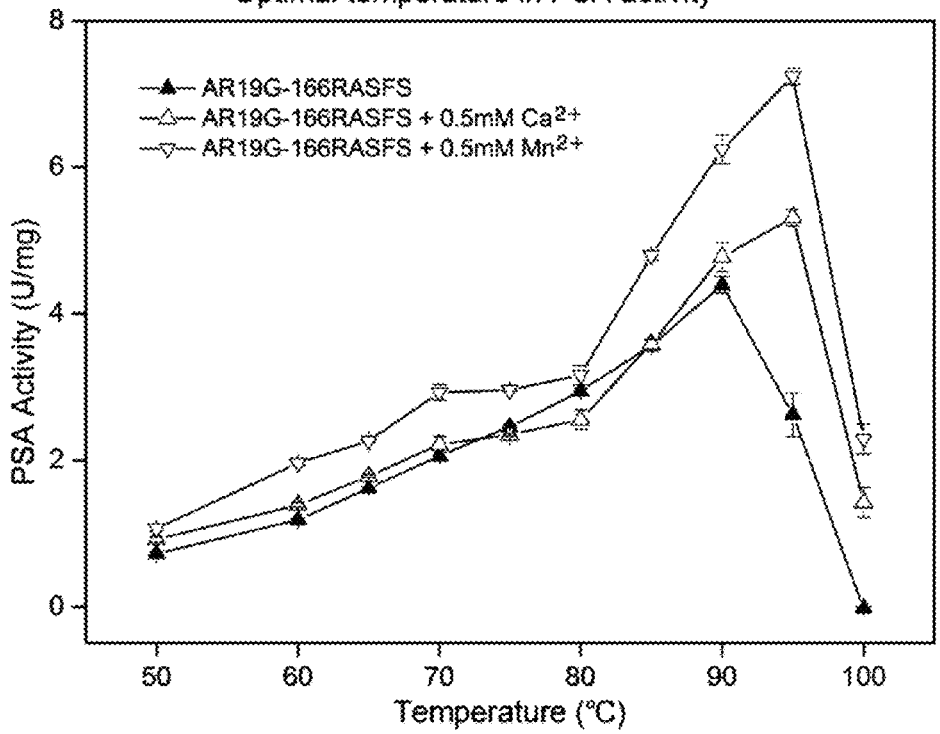
FIG. 5 is a view showing results obtained by measuring the PSA hydrolytic activity of AR19G-166RASFS at the respective temperatures in Example 1.

FIG. 5 shows the measurement results. In the PSA hydrolytic activity of AR19G-166RASFS, $T_{opt}$=90° C. at a pH of 5.5. Moreover, when 0.5 mM calcium ions or 0.5 mM manganese ions were added to the enzyme-substrate reaction liquid, $T_{opt}$ increased to 95° C. in any case. In all of temperature regions, it was confirmed that the addition of the calcium ions or magnesium ions improved the PSA hydrolytic activity. Particularly, the PSA hydrolytic activity at the optimal temperature approximately doubled due to the addition of magnesium ions, and it is considered that this is because the addition of divalent metal cations brought about an effect of stabilizing the enzyme proteins.

(pH Dependency)

Figure 6:
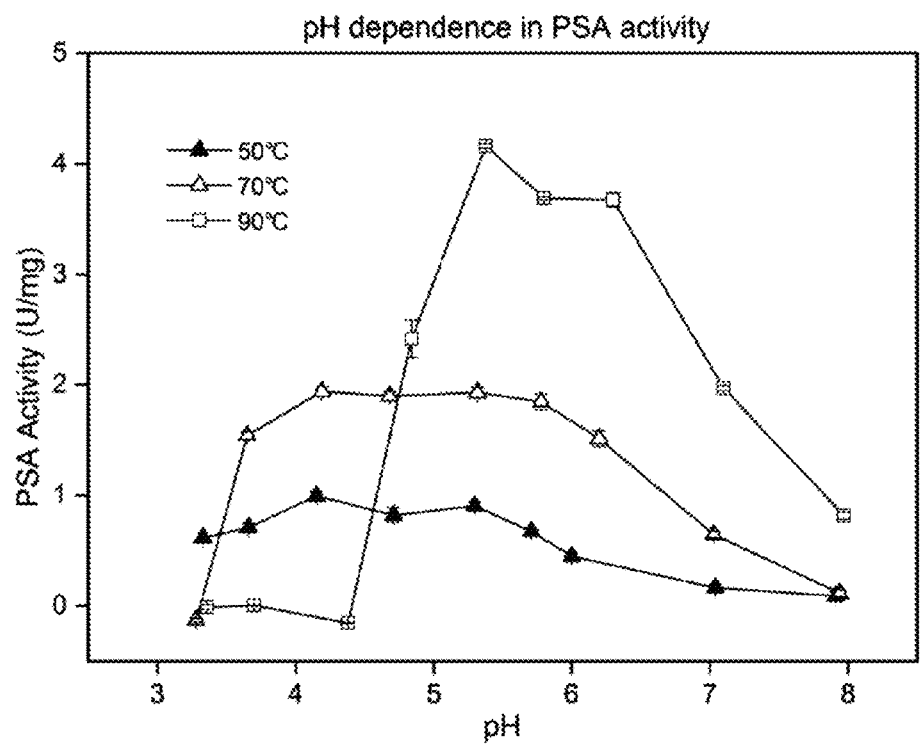
FIG. 6 is a view showing results obtained by measuring the PSA hydrolytic activity (50° C., 70° C., or 90° C.) of AR19G-166RASFS at the respective pH levels in Example 1.

The pH dependency of the PSA hydrolytic activity of AR19G-166RASFS was investigated. For measuring the PSA hydrolytic activity, 0.5% by mass of PSA was used as a substrate; pH of the respective reaction liquids was adjusted by using a Mellvain buffer (a pH of 3 to 8); and the hydrolysis reaction performed at 50° C., 70° C., or 90° C. at each pH level was measured. FIG. 6 shows the measurement results. The PSA hydrolytic activity at 50° C. 70° C., and 90° C. with respect to the actually measured pH level of the reaction liquid was measured and plotted.

As shown in FIG. 6, the optimal pH of the PSA hydrolysis reaction of the purified variant AR19G-166RASFS changed depending on the reaction temperature, and at 90° C., AR19G-166RASFS exhibited the highest PSA hydrolytic activity within a range of a pH of 5 to 6.5. At 50° C. and 70° C., the optimal pH was within a range of a pH of 4 to 6. In any case, a low level of PSA hydrolytic activity was observed at a pH level of equal to or higher than 7.

(Measurement of Heat Stability Using PSA Hydrolytic Activity)

As an index relating to the heat stability of proteins, a thermal denaturation temperature or a melting temperature (Tm) are frequently used. A pre-incubation temperature, at which the enzyme activity is reduced and becomes 50% of the enzyme activity of an untreated section due to preheating (pre-incubation) performed for a certain period of time, is almost the same as the melting temperature $T_m$ of the protein, and can be determined by measuring the enzyme activity. In this manner, the melting temperature $T_m$ of AR19G-166RA and AR19G-166RASFS was determined.

Specifically, by performing preheating for 40 minutes under a substrate-free condition and by using a temperature $T_{50}$, at which the PSA hydrolytic activity reduced 50%, as an index, the heat stability of variant AR19G-166RASFS was investigated. The respective data was subjected to approximation by using a logistic function, and the temperature at which the relative activity level became 50% in the approximated curve was taken as $T_{50}$.

Figure 7:
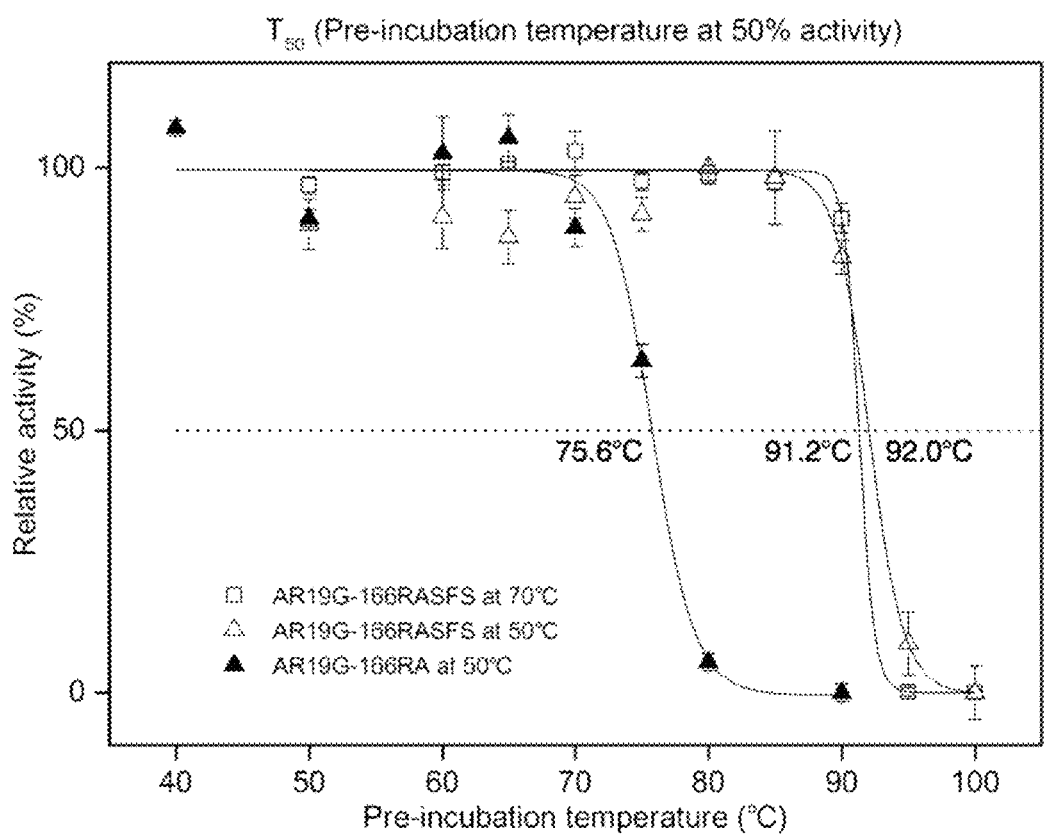
FIG. 7 is a view showing results obtained by measuring a temperature $T_{50}$, at which the PSA hydrolytic activity of AR19G-166RASFS decreases 50% after pre-incubation for 40 minutes, in Example 1.

FIG. 7 shows the measurement results. In AR19G-166RA, $T_{50}$=75.6° C. In contrast, in the variant AR19G-166RASFS in which three amino acid residues substituted, $T_{50}$=91.2° C. (at the time when the PSA activity was measured at 50° C.) or $T_{50}$=92.0° C. (at the time when the PSA activity was measured at 70° C.). AR19G-166RASFS exhibited heat stability of equal to or higher than 15° C. compared to AR19G-166RA.

(Measurement of Heat Stability by DSF Method)

Differential scanning fluorimetry (DSF) is one of the methods for measuring thermal denaturation of proteins by using a fluorescent dye and a real-time PCR device, and can be applied to various proteins. Fluorescent dyes used for DSF, such as SYPRO Orange, fluoresce under a non-polar condition in which the dyes bind to a hydrophobic site, and are inhibited from fluorescing under a polar condition in which the dyes have been dissolved in water. Generally, the folded structure of proteins is opened at a thermal denaturation temperature thereof, and hydrophobic sites in the structure are exposed to the protein surface. When SYPRO Orange binds to the exposed hydrophobic sites, due to excitation light having a wavelength of 470 nm to 480 nm, the dye produces intense fluorescent light having a peak around a wavelength of 595 nm. If the temperature of the protein solution is increased stepwise at a certain interval, and the fluorescence intensity is measured, the melting temperature (=change point of fluorescence intensity) is calculated.

Specifically, 2 μL of SYPRO Orange (manufactured by Life Technologies) diluted 100×, 1 μL of enzyme proteins at a concentration of 1 mg/Ml, 5 μL of 200 mM acetate buffer (a pH of 5.5), and 12 μL of purified water were added to wells of a 96-well PCR plate (Multiplate 96 Well PCR Plate MLL-9651, manufactured by Bio-Rad Laboratories, Inc.), and volume of each well was adjusted to be 20 μL. The PCR plate was sealed with Optical flat 8-cap strips (manufactured by Bio-Rad Laboratories, Inc.), and by using a real-time PCR device (CFX96 Touch Real-Time PCR System, manufactured by Bio-Rad Laboratories, Inc.), the temperature of wells was increased to 100° C. from 30° C. by 0.5° C. After 30 seconds elapsed from when the temperature reached a target temperature, the fluorescence intensity of the respective wells was simultaneously measured. The SYPRO Orange was excited with a light emitting diode (LED)

having a wavelength band of 450 nm to 490 nm, and the light radiated from the SYPRO Orange was caused to pass through a band-pass filter within a range of 560 nm to 580 nm. The fluorescence intensity was measured using a CCD camera, and the change in the fluorescence intensity was plotted in the form of a function of temperature. The thermal denaturation temperature (melting temperature; Tm value) was defined as a maximum value of "−d(Fluorescence)/dt" shown on the ordinate of the graph of the first-order differentiation (lower side of FIG. 8) of the fluorescence intensity curve as a temperature function. By using analysis software CFX Manager (manufactured by Bio-Rad Laboratories, Inc.) included in the real-time PCR device, data analysis was performed. Furthermore, 3 mM calcium ions were added to the respective reaction solutions, and the resultants were measured in the same manner.

Figure 8:
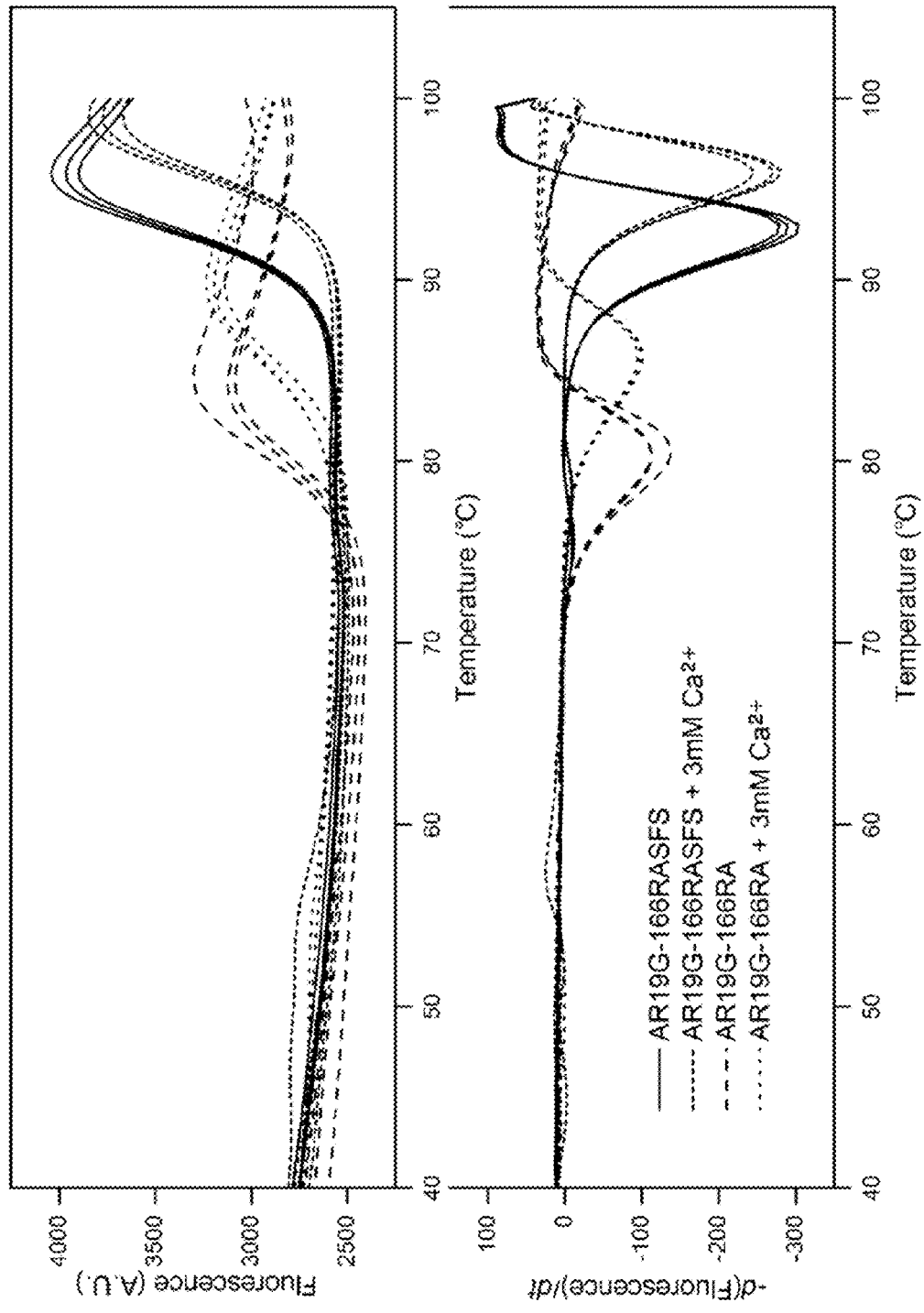
FIG. 8 is a view showing the change in fluorescence intensity of SYPRO Orange that is caused as a result of thermal denaturation of the respective enzyme proteins of AR19G-166RA and AR19G-166RASFS as an amino acid substitution variant of the AR19G-166RA in Example 1.

FIG. 8 shows the change in the fluorescence intensity of the SYPRO Orange that was measured by the DSF method and caused by the thermal denaturation of each of the enzyme proteins of AR19G-166RA and AR19G-166RASFS. The graph in the upper side of FIG. 8 is actually measured data, and the graph in the lower side of FIG. 8 shows the first-order differentiation "−d(Fluorescence)/dt" of the curve of the change in the fluorescence intensity of the graph in the upper side of FIG. 8. Furthermore, by DSF method, the melting temperature of each of the enzyme proteins was measured three times independently. Table 3 shows the average thereof.

TABLE 3

| Enzyme | Melting temperature by DSF (° C., mean ± se) |
| --- | --- |
| AR19G-166RA | 80.5 ± 0.0 (n = 3) |
| AR19G-166RA + 3 mM $Ca^{2+}$ | 85.7 ± 0.2 (n = 3) |
| AR19G-166RASFS | 93.0 ± 0.0 (n = 3) |
| AR19G-166RASFS + 3 mM $Ca^{2+}$ | 96.0 ± 0.0 (n = 3) |

In the DSF fluorescence intensity curve of the enzyme proteins encoded by AR19G-166RASFS, peaks were observed around 95° C. and the thermal denaturation temperature Tm=93.0±0.0 (n=3) (Table 3). The value of the thermal denaturation temperature was close to the optimal temperature $T_{opt}$>90° C. of the enzyme determined from the PSA hydrolytic activity or the enzyme activity halving temperature $T_{50}$=91.2° C. and 92.0° C.

In contrast, in the DSF fluorescence intensity curve of AR19G-166RA, peaks were observed around 83° C., and the $T_m$ value was 80.5±0.0° C. (n=3). This showed that heat stability of AR19G-166RASFS was improved by 12.5° C. as compared with the heat stability of AR19G-166RA.

Divalent metal ions are generally known to stabilize the structure of a protein by binding to the protein and thus improve the thermostability. In AR19G-166RA, due to the addition of 3 mM $Ca^{2+}$, the thermal denaturation temperature Tm calculated by DSF increased by 5.2° C. and became 85.7±0.2° C. (n=3). In AR19G-166RASFS, due to the addition of 3 mM $Ca^{2+}$, Tm increased by 5.2° C. and became 96.0±0.0° C. (n=3). The thermal denaturation temperature 96.0° C. is the highest value for the cellobiohydrolases known so far.

The recalcitrant crystalline cellulose is hydrolyzed into glucose as polysaccharide mainly by cooperation of three kinds of glycoside hydrolases. An endoglucanase (cellulase or endo-1,4-β-D-glucanase, EC 3.2.1.4) randomly cleaves the 1,4-β glycoside bond of a glucan chain, and generates oligosaccharides that are diverse in length. A cellobiohydrolase as an exo-glucanase (1,4-β-cellobiosidase or cellobiohydrolase, EC 3.2.1.91) continuously cleaves a glucan chain from the end thereof that is either a reducing terminal (CBH belonging to a GH17 family, for example, TrCel7A or CBH I) or a non-reducing terminal (CBH belonging to a GH16 family; TrCel6A or CBH II), and generates cellobiose. A β-glucosidase (β-1,4-glucosidase, EC 3.2.1.21) hydrolyzes cellobiose and generates glucose.

To summarize, the above results showed that the variant AR19G-166RASFS formed by substitution of three amino acid residues in AR19G-166RA is a variant which was markedly improved in terms of both the optimal temperature and the thermal denaturation temperature. The results also showed that the enzyme activity halving temperature $T_{50}$, at which the PSA hydrolytic activity is reduced 50%, and the thermal denaturation temperature Tm determined by DSF of the variant were 10.5° C. and 12.5° C. respectively. That is, $T_{50}$ and the $T_m$ of AR19G-166RASFS are high, and it shows that the protein is a variant that has been markedly improved in terms of heat stability.

A large number of super thermostable cellulase enzymes that function at a temperature of equal to or higher than 80° C. has been separated from microorganisms surviving in an extreme environment such as a hydrothermal vent. However, regarding the cellobiohydrolase that exerts the biggest influence on the hydrolysis efficiency, an enzyme having sufficient thermostability has not been obtained. Accordingly, up to now, a super thermostable enzyme mixture liquid that degrades and hydrolyzes lignocellulose biomass at a high temperature that is equal to or higher than 80° C. has not been prepared. If the cellobiohydrolase AR19G-166RASFS having an extremely high degree of thermostability is used, it is possible to prepare an enzyme mixture liquid that enables lignocelluloses to be hydrolyzed by enzymes at a high temperature.

What is claimed is:

1. A method for manufacturing a super thermostable cellobiohydrolase, comprising
a step of culturing a transformant expressing a nucleic acid encoding a cellobiohydrolase domain having a polypeptide of an amino acid sequence equal to or higher than 90% identical to SEQ ID NO: 1, and having serine in the 88$^{th}$ position, phenylalanine in the 230$^{th}$ position and serine in the 414$^{th}$ position of the amino acid sequence,
wherein said super thermostable cellobiohydrolase exhibits cellobiohydrolase activity under conditions of temperature of 80° C. to 100° C. and a pH of 4.0 to a pH of 7.0.

2. A transformant comprising
a nucleic sequence encoding a polypeptide of an amino acid sequence having equal to or higher than 90% identical to SEQ ID NO: 1, having serine in the 88$^{th}$ position, phenylalanine in the 230$^{th}$ position and serine in the 414$^{th}$ position of the amino acid sequence, and having cellobiohydrolase activity under conditions of temperature of 80° C. to 100° C. and a pH of 4.0 to a pH of 7.0.

3. An expression vector comprising
a nucleic sequence encoding a polypeptide of an amino acid sequence having equal to or higher than 90% identical to SEQ ID NO: 1, having serine in the 88$^{th}$ position, phenylalanine in the 230$^{th}$ position and serine in the 414$^{th}$ position of the amino acid sequence, and having cellobiohydrolase activity under conditions of temperature of 80° C. to 100° C. and a pH of 4.0 to a pH of 7.0.

* * * * *